(12) United States Patent
Wang et al.

(10) Patent No.: US 10,329,510 B2
(45) Date of Patent: Jun. 25, 2019

(54) SELF-HEALABLE COATINGS AND METHODS OF MAKING THE SAME

(71) Applicant: The Penn State Research Foundation, University Park, PA (US)

(72) Inventors: Jing Wang, State College, PA (US); Tak-Sing Wong, State College, PA (US)

(73) Assignee: THE PENN STATE RESEARCH FOUNDATION, University Park, PA (US)

( * ) Notice: Subject to any disclaimer, the term of this patent is extended or adjusted under 35 U.S.C. 154(b) by 101 days.

(21) Appl. No.: 15/302,315

(22) PCT Filed: Apr. 10, 2015

(86) PCT No.: PCT/US2015/025422
§ 371 (c)(1),
(2) Date: Oct. 6, 2016

(87) PCT Pub. No.: WO2015/199791
PCT Pub. Date: Dec. 30, 2015

(65) Prior Publication Data
US 2017/0121624 A1    May 4, 2017

Related U.S. Application Data

(60) Provisional application No. 61/978,578, filed on Apr. 11, 2014.

(51) Int. Cl.
*C09D 5/00*    (2006.01)
*C09D 7/63*    (2018.01)
(Continued)

(52) U.S. Cl.
CPC ........... *C10M 107/50* (2013.01); *A01N 25/08* (2013.01); *C09D 5/00* (2013.01); *C10M 105/76* (2013.01);
(Continued)

(58) Field of Classification Search
CPC ............ C10M 105/76; C10M 2211/06; C10M 2213/04; C10M 2227/04
See application file for complete search history.

(56) References Cited

U.S. PATENT DOCUMENTS

2014/0037964 A1* 2/2014 Zheng ................. G02B 1/04
428/412

FOREIGN PATENT DOCUMENTS

WO    2012/100099 A2    7/2012

OTHER PUBLICATIONS

Sunny et al., Lubricant-Infused Nanoparticles Coatings Assembled by Layer-by-Layer Deposition, Adv. Funct. Mater., vol. 24, No. 42, Sep. 1, 2014, pp. 6658-6667 [retrieved online Nov. 25, 2015].
(Continued)

*Primary Examiner* — Ramsey Zacharia
(74) *Attorney, Agent, or Firm* — Morgan Lewis & Bockius LLP

(57) ABSTRACT

A robust and self-healing coating has been developed by incorporating a thermally self-healing chemical coating on smooth and/or roughened solid. When the chemically coated solid is combined with a lubricating fluid, the material system is capable to repel a broad range of liquids and solids. The thermally self-healing chemical coating may be applied on various industrial metals, glass and plastics, and has shown exceptionally physical and chemical robustness as compared to state-of-the-art liquid-repellent coatings.

20 Claims, 22 Drawing Sheets

(51) Int. Cl.
*B05D 3/04* (2006.01)
*C10M 107/50* (2006.01)
*A01N 25/08* (2006.01)
*C10M 105/76* (2006.01)
*B05D 3/00* (2006.01)

(52) U.S. Cl.
CPC ................ *B05D 3/007* (2013.01); *B05D 3/04* (2013.01); *C09D 7/63* (2018.01); *C10M 2227/04* (2013.01)

(56) References Cited

OTHER PUBLICATIONS

Wong et al., "Bioinpired self-repairing slippery surfaces with pressure-stable omniphobicity," Nature, vol. 477, Sep. 22, 2011, pp. 443-447 [online] [ retrieved on Nov. 25, 2015].
International Search Report and Written Opinion, issued in Application No. PCT/US2015/025422, dated Dec. 30, 2015.

\* cited by examiner

SELF-HEALABLE COATINGS AND METHODS OF MAKING THE SAME

CROSS-REFERENCE TO RELATED APPLICATIONS

This application is the U.S. National Phase under 35 U.S.C. § 371 of International Application No. PCT/US2015/025422, filed Apr. 10, 2015, which claims priority to U.S. Provisional Application No. 61/978,578, filed on Apr. 11, 2014, which is incorporated fully herein by reference.

STATEMENT REGARDING FEDERALLY SPONSORED RESEARCH

This invention was made with government support under Advanced Research Projects Agency-Energy of U.S. Department of Energy (DE-AR0000326), Office of Naval Research (N00014-12-1-0875), and the National Science Foundation (Award#: 1351462). The United States government has certain rights in the invention.

INTRODUCTION

Materials that have the ability to self-heal are sought for a variety of applications.

SUMMARY

In one embodiment, provided are articles comprising the self-healing coatings. The article may comprise a substrate, a self-healable coating adhered to the substrate, the self-healable coating comprising silane molecules having a length and the coating having a thickness at least five times greater than the length of the silane molecules, the coating being self-healing such that when the coating is damaged to form a damaged portion, the damaged portion heals itself when exposed to a temperature of about 40° C. to about 400° C. for a period of time, and lubricant The lubricant may not form an interface with the substrate. The substrate may comprise a roughened surface. The self-healing coating may be covalently bonded to the substrate. The self-healable coating may be about 2 nm to about 10 µm. The substrate may include at least one of a polymer, plastics, metal, sapphire, optically transparent material including glass (e.g. on a window), carbon in different form, or ceramic. The silane molecule may include (heptadecafluoro-1,1,2,2-tetrahydrodecyl), trichlorosilane, tridecafluoro-1,1,2,2-tetra-hydrodecyl triethoxysilane, 4-bromo-3,3,4,4-tetrafluorobutyltrichlorosilane, (heptadecafluoro-1,1,2,2-tetrahydrodecyl) methyldechlorosilane, 1H,1H,2H,2H-perfluorooctyl phosphonic acid(3-heptafluotoisopropoxy)propyltrichlorosilane, (3-Chloropropyl)trimethoxysilane, polytetrafluoroethylene, octadecyltrichlorosilane, nonafluoro hexyl trimethoxysilane and combinations thereof. The lubricant may include tertiary perfluoroalkylamines, perfluoroalkylsulfides, perfluoroalkylsulfoxides, perfluoroalkylethers, perfluorocycloethers, perfluoropolyethers, perfluoroalkylphosphines, perfluoroalkylphosphineoxides, mineral oils, plant oils, ionic liquids, liquid polydimethysiloxane, water, aqueous liquids, hydrocarbons and combinations thereof.

The article may heal its damaged portions when exposed to a temperature of above 40° C. In certain embodiments, the article has repellency to high surface tension and/or low surface tension liquids and/or solid substances. The high surface tension liquid may be water. The low surface tension liquid may be an aqueous liquid comprising surfactants and/or organic liquids. In certain embodiments, the article may have repellency to complex fluids. The complex fluids may include biological fluids and/or crude oil. The solids may include biological and/or non-biological substances. The biological substances may include bacteria and/or insects. The non-biological substances may include ice.

The article may have a contact angle hysteresis for a repelled liquid less than about 5°. The article may have a slide-off angle for a repelled liquid less than about 5°. In certain embodiments, the article may be able to withstand at least 50 pressure sensitive tape attachment-and-detachment tests with at least a force of 0.5 N.

In another aspect, provided are uses for articles comprising the self-healing coating. The article may include engines, hypodermal needles, heat exchangers, windows and other optically transparent materials, rotating parts, and/or airfoils. The rotating parts may be ball bearings and/or gears.

In another aspect, provided are methods of producing a self-healing coating on a substrate. The method may comprise applying a composition comprising silane molecules to at least a portion of the substrate to form a coating thereon, the silane molecules having a length and the coating having a thickness that is at least five times greater than the length of the silane molecules, the coating being self-healing such that when the coating is damaged to form a damaged portion, the damaged portion heals itself when exposed to a temperature of about 40° C. to about 400° C. for a period of time. The method may further comprise lubricating the coating with a liquid or gaseous lubricant having affinity for the coating. The method may include roughening the surface of the substrate. The method may further include alcohol. Applying the composition may be done in the liquid or vapor phase. Additionally, applying the composition may be done for at least 5 hours at room temperature. In certain embodiments, applying the composition may be done for at least 1 hour at 80° C. The coating may also be covalently bonded to the substrate.

In another aspect, provided are types of coatings produced by the method for producing a self-healing coating. The types of coating include, but are not limited to, anti-icing coating, drag-reduction coating, anti-fouling coating, anti-graffiti coating, anti-scaling coating, and/or insect-repellent coating.

The self-healing coating produced from the above method may have a thickness of about 2 nm to about 10 µm. The coating may include at least one of a polymer, plastics, metal, sapphire, glass, carbon in different form, or ceramic. The coating may include a silane molecule selected from (heptadecafluoro-1,1,2,2-tetra-hydrodecyl)trichlorosilane, tridecafluoro-1,1,2,2-tetra-hydrodecyl triethoxysilane, 4-bromo-3,3,4,4-tetrafluorobutyltrichlorosilane, (heptadecafluoro-1,1,2,2-tetrahydrodecyl)methyldechlorosilane, 1H,1H,2H,2H-perfluorooctyl phosphonic acid(3-heptafluotoisopropoxy)propyltrichlorosilane, (3-Chloropropyl)trimethoxysilane, polytetrafluoroethylene, octadecyltrichlorosilane, nonafluoro hexyl trimethoxysilane, and combinations thereof. The coating may include a lubricant selected from tertiary perfluoroalkylamines, perfluoroalkylsulfides, perfluoroalkylsulfoxides, perfluoroalkylethers, perfluorocycloethers, perfluoropolyethers, perfluoroalkylphosphines, perfluoroalkylphosphineoxides, mineral oils, plant oils, ionic liquids, liquid polydimethysiloxane, water, aqueous liquids, and hydrocarbons, and combinations thereof. In certain embodiments, lubricating the coating is performed by spraying, dip coating, spinning, rubbing from an oil-infused fabric, and combinations thereof. In certain embodiments, the coating may be able to self-heal at least 16 times.

Other aspects of the invention will become apparent by consideration of the detailed description and accompanying drawings.

DETAILED DESCRIPTION

Figure 1:
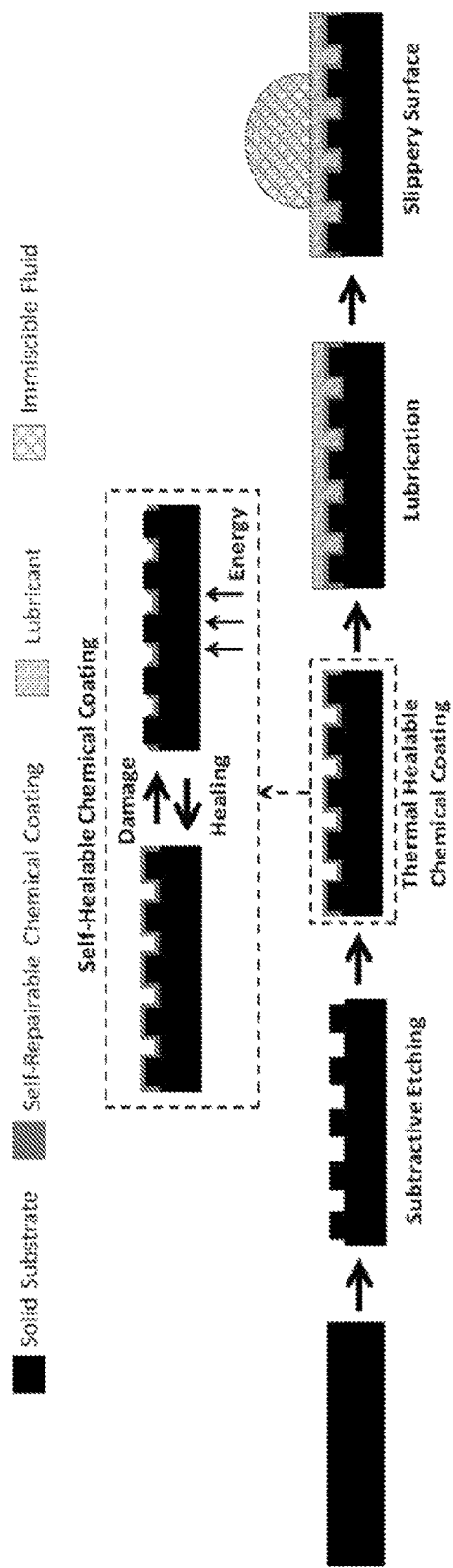
FIG. 1 displays a general manufacturing schematic for producing one embodiment of the self-healing coating onto a substrate.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

State-of-the-art liquid repellent surfaces are primarily modeled after lotus leaves, springtails, and pitcher plants. Each of these natural species utilizes a different physical mechanism for liquid repellency. In lotus leaves, micro/nanoscale hierarchical physical textures with low-surface-energy chemical coatings are utilized to entrap a thin layer of air, which then acts as an air cushion against any impacting water droplets. Since the water droplets are mostly supported by the air-layer with minimal contacts with the hydrophobic solid textures, these water droplets form a nearly spherical shape and may be rolled off from the surface easily. Springtails, which are arthropods that live in the soil, have evolved overhanging nanostructured skin patterns that help prevent soiling and resist wetting by organic liquids. On the other hand, the rim of pitcher plants utilizes the microscale physical textures with high-surface-energy chemical coatings to entrap a thin layer of liquid lubricating film such as water, which then acts as a liquid cushion to repel any foreign fluids/objects that are immiscible with the film. Since the lubricating film is intrinsically smooth down to molecular scale, it eliminates pinning of the foreign immiscible fluids which enhance their mobility on the surface. A synthetic surface inspired by this mechanism was recently developed, and is known as slippery pre-suffused surfaces. Despite the difference in the liquid repellency mechanisms, many of these natural species capitalize the ideas of physical textures and chemical coatings to ultimately achieve liquid repellency. Translating these natural concepts into artificial surfaces for practical applications would require physical and chemical robustness, particularly under harsh environments. As a result, the ability to self-heal either or both of the physical textures and chemical coatings are of fundamental importance for the continuous operations of these artificial liquid-repellent surfaces.

1. Self-Healing Coating

Disclosed herein are self-healing coatings that may be used for a variety of applications. The self-healing coating may comprise a substrate, a chemical coating and a lubricant. The self-healing coating may be used as part of an article.

The coatings of the present disclosure may self-heal themselves upon physical or chemical damage to a surface of the substrate. That is, the so-called damaged portion is a portion of the coating in which the chemical coating and lubricant have been removed, for example due to physical abrasion of the surface of the coating. The damage of this portion may be seen as a region in which the properties conferred by the self-healing coating, e.g. hydrophobicity, are lacking. Self-healing in this context may include the reintroduction of the chemical coating (e.g. by heating of the article) to the damaged portion and subsequent restoration of the properties conferred by the chemical coating and lubricant (e.g. restoration of hydrophobicity). Without being limited by theory, it is believed that treatments of the article such as heating cause the chemical coating to redistribute over the damaged area (from which the lubricant and chemical coating may have been removed due to physical abrasion or other causes). Exposing coatings to elevated temperatures for a period of time may result in the coatings self-healing. The self-healing coatings may have the ability to self-heal when heated to a temperature of about 40° C. to about 400° C. for a period of time of about 10 seconds to about 300 minutes. For example, the coating may self-heal if they are heated to a temperature of at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., at least 105° C., at least 110° C., at least 115° C., at least 120° C., at least 125° C., at least 130° C., at least 135° C., at least 140° C., at least 145° C., at least 150° C., at least 155° C., at least 160° C., at least 165° C., at least 170° C., at least 175° C., at least 180° C., at least 185° C., at least 190° C., at least 195° C., at least 200° C., at least 205° C., at least 210° C., at least 215° C., at least 220° C., at least 225° C., at least 230° C., at least 235° C., at least 240° C., at least 245° C., at least 250° C., at least 255° C., at least 260° C., at least 265° C., at least 270° C., at least 275° C., at least 280° C., at least 285° C., at least 290° C., at least 295° C., at least 300° C., at least 305° C., at least 310° C., at least 315° C., at least 320° C., at least 325° C., at least 330° C., at least 335° C., at least 340° C., at least 345° C., at least 350° C., at least 355° C., at least 360° C., at least 365° C., at least 370° C., at least 375° C., at least 380° C., at least 385° C., at least 390° C., at least 395° C., or at least 400° C.

Additionally, the coating may self-heal if they are heated to a temperature of less than 400° C., less than 395° C., less than 390° C., less than 385° C., less than 380° C., less than 375° C., less than 370° C., less than 365° C., less than 360° C., less than 355° C., less than 350° C., less than 345° C., less than 340° C., less than 335° C., less than 330° C., less than 325° C., less than 320° C., less than 315° C., less than 310° C., less than 305° C., less than 300° C., less than 295° C., less than 290° C., less than 285° C., less than 280° C., less than 275° C., less than 270° C., less than 265° C., less than 260° C., less than 255° C., less than 250° C., less than 245° C., less than 240° C., less than 235° C., less than 230° C., less than 225° C., less than 220° C., less than 215° C., less than 210° C., less than 205° C., less than 200° C., less than 195° C., less than 190° C., less than 185° C., less than 180° C., less than 175° C., less than 170° C., less than 165° C., less than 160° C., less than 155° C., less than 150° C., less than 145° C., less than 140° C., less than 135° C., less than 130° C., less than 125° C., less than 120° C., less than 115° C., less than 110° C., less than 105° C., less than 100° C., less than 95° C., less than 90° C., less than 85° C., less than 80° C., less than 75° C., less than 70° C., less than 65° C., less than 60° C., less than 55° C., less than 50° C., less than 45° C., or less than 40° C.

In some embodiments, wherein the substrate comprises a plastic, the preferred range of the temperature used for performing the self-healing is from about 75° C. to about 100° C., and in this range, the healing time is generally less than 75 min. In some embodiments, wherein the substrate comprises metals, glass and/or ceramics, the preferred range for the temperature used to perform the self-healing is from about 120° C. to about 200° C. and in this range, the healing time is typically less than 5 min.

The time it may take for the self-healing coating to self-heal may be at least 10 seconds, at least 20 seconds, at least 30 seconds, at least 40 seconds, at least 50 seconds, at least 60 seconds, at least 2 minutes, at least 3 minutes, at least 4 minutes, at least 5 minutes, at least 6 minutes, at least 7 minutes, at least 8 minutes, at least 9 minutes, at least 10 minutes, at least 11 minutes, at least 12 minutes, at least 13 minutes, at least 14 minutes, at least 15 minutes, at least 16 minutes, at least 17 minutes, at least 18 minutes, at least 19 minutes, at least 20 minutes, at least 21 minutes, at least 22 minutes, at least 23 minutes, at least 24 minutes, at least 25 minutes, at least 26 minutes, at least 27 minutes, at least 28 minutes, at least 29 minutes, at least 30 minutes, at least 60 minutes, at least 100 minutes, at least 200 minutes, or at least 300 minutes.

Additionally, the time it may take for the self-healing coating to self-heal may be less than 300 minutes, less than 200 minutes, less than 100 minutes, less than 60 minutes, less than 30 minutes, less than 29 minutes, less than 28 minutes, less than 27 minutes, less than 26 minutes, less than 25 minutes, less than 24 minutes, less than 23 minutes, less than 22 minutes, less than 21 minutes, less than 20 minutes, less than 19 minutes, less than 18 minutes, less than 17 minutes, less than 16 minutes, less than 15 minutes, less than 14 minutes, less than 13 minutes, less than 12 minutes, less than 11 minutes, less than 10 minutes, less than 9 minutes, less than 8 minutes, less than 7 minutes, less than 6 minutes, less than 5 minutes, less than 4 minutes, less than 3 minutes, less than 2 minutes, less than 60 seconds, less than 50 seconds, less than 40 seconds, less than 30 seconds, less than 20 seconds, or less than 10 seconds.

The self-healing coating may comprise enhanced robustness. For example, the coatings may have the ability to self-heal at least the following number of times: 1, 2, 3, 4, 5, 6, 7, 8, 9, 10, 11, 12, 13, 14, 15, 16, 17, 18, 19 or 20. The coating may be able to withstand at least 50, at least 49, at least 48, at least 47, at least 46, at least 45, at least 44, at least 43, at least 42, at least 41, at least 40, at least 39, at least 38, at least 37, at least 36, at least 35, at least 34, at least 33, at least 32, at least 31, at least 30, at least 29, at least 28, at least 27, at least 26, at least 25, at least 24, at least 23, at least 22, at least 21, at least 20, at least 19, at least 18, at least 17, at least 16, at least 15, at least 14, at least 13, at least 12, at least 11, at least 10, at least 9, at least 8, at least 7, at least 6, at least 5, at least 4, at least 3, at least 2 or at least 1 pressure sensitive tape attachment-and-detachment tests at a force of at least 0.5 N, at least 0.4 N, at least 0.3 N, at least 0.2 N or at least 0.1 N. The number of pressure sensitive tape attachment-and-detachment cycles may be dependent on the force used to perform the test.

A. Substrate

The self-healing coating may comprise a substrate. The substrate may include, but is not limited to polymer, plastic, metal, sapphire, glass, carbon in different form, ceramic or combinations thereof. The polymer may be, but is not limited to, polyethylene, high density polyethylene, low density polyethylene, polycarbonate, polyurethanes, or polypropylene. The metal may be, but is not limited to, aluminum, iron, stainless steel, titanium, brass, bronze, copper, or metal alloys. The substrate may be roughened. Substrate roughening is optional and may be used when additional roughness is required to enhance the liquid repellency. To create surface roughness on substrates, both additive deposition and subtractive etching may be used.

Additive deposition refers to the addition of materials onto the substrate to form roughness, typical additive deposition includes, but is not limited to, spray coating, electro-deposition, chemical vapor deposition, laser deposition etc. Physical robustness of the surface textures may be dependent on the adhesion between the added materials and the base substrate.

Subtractive etching refers to the removing of excess materials from the surface to create roughness, which include chemical etching (e.g., reactive ion etching, or liquid/vapor etching) and physical etching (e.g., sand blasting, or abrasion). Physical robustness of the surface textures is relatively stronger as the surface textures may be mono-lithographically integrated within the base substrate. For example, a combination of ferric chloride and hydrochloric acid may be used to etch stainless steel (304, 316, carbon steel) and copper for a surface roughness on the order of 500 nm to 100 µm; condensed hydrochloric acid at room temperature, as well as diluted hydrochloric acid may be used to etch titanium and aluminum to create roughness on the order of 50 nm to 100 µm; water vapor may be used to directly etch aluminum to create roughness on the order of less than 100 nm to 500 nm; a combination of hydrofluoric and hydrochloric acids may be used to etch glass. The surface roughness of the resulting etched surfaces is dependent on the grain size of the respective materials and the etching time. Typically, the etching time may be from about 15 minutes to more than an hour. For example, the etching time may be at least 15 min, at least 16 min, at least 17 min, at least 18 min, at least 19 min, at least 20 min, at least 21 min, at least 22 min, at least 23 min, at least 24 min, at least 25 min, at least 26 min, at least 27 min, at least 28 min, at least 29 min, at least 30 min, at least 31 min, at least 32 min, at least 33 min, at least 34 min, at least 35 min, at least 36 min, at least 37 min, at least 38 min, at least 39 min, at least 40 min, at least 41 min, at least 42 min, at least 43 min, at least 44 min, at least 45 min, at least 46 min, at least 47 min, at least 48 min, at least 49 min, at least 50 min, at least 51 min, at least 52 min, at least 53 min, at least 54 min, at least 55 min, at least 56 min, at least 57 min, at least 58 min, at least 59 min, or at least 1 hour.

In some embodiments, the etching method may provide sub-100 nm roughness. For example, etching on a glass can form nano-structures by immersing the glass into 0.5 mol/L of sodium bicarbonate water solution, and then placing the mixture onto a hot plate at 300° C. for approximately 24 hours. The resultant surface is etched with about a 10 nm to about 30 nm nano porous structure.

In some embodiments, a suitable chemical etchant is used to etch the substrate and create surface roughness on the order of 100 nm to 100 µm (FIG. 6-10).

TABLE 1

Subtractive etching of metals to create micro- and nanostructures

| Materials | Etchants | Typical Dimensions |
|---|---|---|
| Stainless Steel (304, 316, S/5, S10, etc.) | Ferric chloride/hydrochloric acid | 500 nm-100 µm |
| Carbon Steel | Ferric chloride/hydrochloric acid | 500 nm-100 µm |
| Titanium | Concentrated hydrochloric acid | 100 nm to 100 µm |
| Copper | Ferric chloride/hydrochloric acid | 500 nm-100 µm |
| Aluminum | Dilute hydrochloric acid/heated water vapor | 50 nm to 500 nm |
| Glass | Hydrofluoric acid/sodium bicarbonate water olution | 100 nm to 100 µm |

B. Silane Coating

The self-healing coating may comprise a chemical coating. The chemical coating may be a silane coating. The silane coating may form covalent bonds with the substrate. The silane coating may have a strong chemical affinity to a lubricant, which alone or in combination with the lubricant, may be able to repel a broad range of liquids and solids. The silane coating may include (heptadecafluoro-1,1,2,2-tetrahydrodecyl), trichlorosilane, tridecafluoro-1,1,2,2-tetra-hydrodecyl triethoxysilane, 4-bromo-3,3,4,4-tetrafluorobutyl-trichlorosilane, (heptadecafluoro-1,1,2,2-tetrahydrodecyl) methyldechlorosilane, 1H,1H,2H,2H-perfluorooctyl phosphonic acid(3-heptafluotoisopropoxy)propyltrichlo-rosilane, (3-Chloropropyl)trimethoxysilane, polytetrafluoro-ethylene, octadecyltrichlorosilane, nonafluoro hexyl trimethoxysilane, heptadecaflourodecyltrimethoxysilane, octadecyldimethylchlorosilane, octyldimethylchlorosilane, dimethyldichlorosilane, butyldimethylchlorosilane, trimethylchlorosilane, and/or combinations thereof. The silane coating may be tuned to meet the needs of different applications, thereby creating tailored surfaces for specific applications. For example, the silane coating may provide a surface that is hydrophilic, hydrophobic, oleophilic, oleophobic, or combinations thereof. In embodiments where the silane coating is hydrophobic and/or oleophilic, the silane's silicon group may bond with chloride and hydrophobic groups.

The silane coating comprises silane molecules. A typical silane molecule has a characteristic length of $L_{mono}$, which is dependent on the functional group that is attached to the molecule. Conventional surface modification would only require the chemical coating of thickness on the order of $L_{mono}$, or monolayer, to achieve the intended surface property. However, the self-healable chemical coating may have a thickness, $L_{coating}$, which is much greater than $L_{mono}$. For example, $L_{coating}$ may be at least 2 times greater than $L_{mono}$, at least 3 times greater than $L_{mono}$, at least 4 times greater than $L_{mono}$, at least 5 times greater than $L_{mono}$, at least 6 times greater than $L_{mono}$, at least 7 times greater than $L_{mono}$, at least 8 times greater than $L_{mono}$, at least 9 times greater than $L_{mono}$, at least 10 times greater than $L_{mono}$, at least 11 times greater than $L_{mono}$, at least 12 times greater than $L_{mono}$, at least 13 times greater than $L_{mono}$, at least 14 times greater than $L_{mono}$, at least 15 times greater than $L_{mono}$, at least 16 times greater than $L_{mono}$, at least 17 times greater than $L_{mono}$, at least 18 times greater than $L_{mono}$, at least 19 times greater than $L_{mono}$, at least 20 times greater than $L_{mono}$, at least 21 times greater than $L_{mono}$, at least 22 times greater than $L_{mono}$, at least 23 times greater than $L_{mono}$, at least 24 times greater than $L_{mono}$, at least 25 times greater than $L_{mono}$, at least 26 times greater than $L_{mono}$, at least 27 times greater than $L_{mono}$, at least 28 times greater than $L_{mono}$, at least 29 times greater than $L_{mono}$, at least 30 times greater than $L_{mono}$, at least 31 times greater than $L_{mono}$, at least 32 times greater than $L_{mono}$, at least 33 times greater than $L_{mono}$, at least 34 times greater than $L_{mono}$, at least 35 times greater than $L_{mono}$, at least 36 times greater than $L_{mono}$, at least 37 times greater than $L_{mono}$, at least 38 times greater than $L_{mono}$, at least 39 times greater than $L_{mono}$, at least 40 times greater than $L_{mono}$, at least 41 times greater than $L_{mono}$, at least 42 times greater than $L_{mono}$, at least 43 times greater than $L_{mono}$, at least 44 times greater than $L_{mono}$, at least 45 times greater than $L_{mono}$, at least 46 times greater than $L_{mono}$, at least 47 times greater than $L_{mono}$, at least 48 times greater than $L_{mono}$, at least 49 times greater than $L_{mono}$ at least 50 times greater than $L_{mono}$, at least 51 times greater than $L_{mono}$, at least 52 times greater than $L_{mono}$, at least 53 times greater than $L_{mono}$, at least 54 times greater than $L_{mono}$, at least 55 times greater than $L_{mono}$, at least 56 times greater than $L_{mono}$ at least 57 times greater than $L_{mono}$, at least 58 times greater than $L_{mono}$, at least 59 times greater than $L_{mono}$, at least 60 times greater than $L_{mono}$, at least 61 times greater than $L_{mono}$, at least 62 times greater than $L_{mono}$, at least 63 times greater than $L_{mono}$, at least 64 times greater than $L_{mono}$, at least 65 times greater than $L_{mono}$, at least 66 times greater than $L_{mono}$, at least 67 times greater than $L_{mono}$, at least 68 times greater than $L_{mono}$, at least 69 times greater than $L_{mono}$, at least 70 times greater than $L_{mono}$, at least 71 times greater than $L_{mono}$, at least 72 times greater than $L_{mono}$, at least 73 times greater than $L_{mono}$, at least 74 times greater than $L_{mono}$, at least 75 times greater than $L_{mono}$, at least 76 times greater than $L_{mono}$, at least 77 times greater than $L_{mono}$ at least 78 times greater than $L_{mono}$, at least 79 times greater than $L_{mono}$, at least 80 times greater than $L_{mono}$, at least 81 times greater than $L_{mono}$, at least 82 times greater than $L_{mono}$, at least 83 times greater than $L_{mono}$, at least 84 times greater than $L_{mono}$ at least 85 times greater than $L_{mono}$, at least 86 times greater than $L_{mono}$, at least 87 times greater than $L_{mono}$, at least 88 times greater than $L_{mono}$, at least 89 times greater than $L_{mono}$, at least 90 times greater than $L_{mono}$, at least 91 times greater than $L_{mono}$, at least 92 times greater than $L_{mono}$, at least 93 times greater than $L_{mono}$, at least 94 times greater than $L_{mono}$, at least 95 times greater than $L_{mono}$, at least 96 times greater than $L_{mono}$, at least 97 times greater than $L_{mono}$, at least 98 times greater than $L_{mono}$, at least 99 times greater than $L_{mono}$, or at least 100 times greater than $L_{mono}$.

The silane coating on the substrate may have the ability to self-heal. Upon physical or chemical damage to the surface of a silane-coated substrate, the silane coating may heal itself when exposed to increased temperatures. In some embodiments, self-healing comprises that the coating has a contact angle hysteresis of less than 5° before being damaged, and then also following the self-healing process. To damage the chemical coating of the surface, one may either physically abrade the surface or perform chemical etching such as oxygen plasma. Both methods will remove the silane layer on the apex of the surface structures, and leave some silane layers at the valleys of the surface structures. It is hypothesized, without being bound to any particular theory, that when the substrate is heated, the silane molecules in the valley may gain additional thermal energy, and may start to migrate or evaporate and redistribute on the surface in order to minimize the surface energy of the exposed region. Accordingly, the redistributed silane molecules may form a covalent bond with the substrate at the exposed region, restoring the chemical coating. Additionally, the silane coating may heal itself either in the presence of the lubricant or when the lubricant is not present. When the lubricant is present, it is hypothesized, without being bound to any particular theory, that when the substrate is heated, the silane molecules and the lubricant may gain additional thermal energy, and may start to migrate or evaporate and redistribute on the surface in order to minimize the surface energy of the exposed region. The lubricant may migrate with the silane molecules, may migrate after the silane molecules have formed a covalent bond with the substrate, or at kinetics in between.

TABLE 2

Time deposition of silane chemical coatings

| Materials | Deposition Methods | Deposition Conditions |
| --- | --- | --- |
| Stainless Steel (304, 316) | Liquid phase: silane/ethanol | Time: 15 to 30 hours Temperature: room temperature to 80° C. |
| Carbon Steel | Liquid phase: silane/ethanol | Time: 15 to 30 hours Temperature: room temperature to 80° C. |
| Titanium | Liquid phase: silane/ethanol | Time: 15 to 30 hours Temperature: room temperature to 80° C. |
| Copper | Liquid phase: silane/ethanol | Time: 15 to 30 hours Temperature: room temperature to 80° C. |
| Aluminum | Liquid phase: silane/ethanol | Time: 15 to 30 hours Temperature: room temperature to 80° C. |
| Glass | Liquid phase: silane/ethanol; Gas phase: | Time: 15 to 30 hours Temperature: room temperature to 80° C. |
| Plastics | Liquid phase: silane/ethanol; Gas phase: | Time: 15 to 30 hours Temperature: room temperature to 80° C. |

C. Lubricant

The self-healing coating may comprise a lubricant. The self-healing coating may be self-healed in the presence of the lubricant or when the lubricant is not present. In embodiments wherein self-healing is performed in the presence of the lubricant, the temperature used to self-heal may be less than the boiling point of the lubricant. The lubricant may instill further surface properties of the self-healing coating. For example, the lubricant may provide a surface that is hydrophilic, hydrophobic, oleophilic, oleophobic, or combinations thereof. The lubricant may or may not form an interface with the substrate. The chemical coated substrate may be lubricated by either air or a liquid. For lubrication with air, the chemical coating on the optionally roughened substrate may be hydrophobic in order to create a surface that repels aqueous liquids. For lubrication with a liquid, typical lubricants include, but are not limited to, tertiary perfluoroalkylamines, perfluoroalkylsulfides, perfluoroalkylsulfoxides, perfluoroalkylethers, perfluorocycloethers, perfluoropolyethers, perfluoroalkylphosphines, perfluoroalkylphosphineoxides, mineral oils, plant oils, ionic liquids, liquid polydimethysiloxane, water, aqueous liquids, hydrocarbons and combinations thereof. In some embodiments, silanes are not used as the lubricant.

For lubrication with a liquid, the liquid should satisfy two conditions: 1) the lubricant should be immiscible with the foreign liquids or solids to be repelled; 2) the self-healing coating may be preferentially wetted by the lubricating liquid rather than by the liquid one wants to repel. To form a stable lubricating film that is not displaced by the foreign liquid, the chemical and physical properties required for working combinations of substrates and lubricants may be engineered. More specifically, the following engineering criteria has been derived to ensure the self-healing coating is wetted preferentially by the lubricating fluid:

$$\Delta E_1 = R(\gamma_B \cos \theta_B - \gamma_A \cos \theta_A) - \gamma_{AB} > 0, \quad \text{(eq.1)}$$

$$\Delta E_2 = R(\gamma_B \cos \theta_B - \gamma_A \cos \theta_A) + \gamma_A - \gamma_B > 0, \quad \text{(eq.2)}$$

where $\gamma_A$ and $\gamma_B$ are the surface tensions for the test liquid (Liquid A) and the lubricating fluid to be repelled, respectively; $\gamma_{AB}$ is the interfacial tension at the liquid-liquid interface of the test liquid and the lubricating fluid; $\theta_A$ and $\theta_B$ are the equilibrium contact angles of the immiscible liquid and the lubricant on a flat solid surface; and R is the roughness factor, e.g., the ratio between the actual and projected surface areas of the self-healable coating.

Based on the engineering criteria, a suitable chemical functionalization scheme may be selected along with the lubricant for repellency of various foreign liquids (Table 3):

TABLE 3

Selection of lubricant and chemical coatings for the slippery surfaces

| Chemical Coating | Lubricant | Foreign Liquids |
|---|---|---|
| (heptadecafluoro-1,1,2,2-tetra-hydrodecyl) trichlorosilane, tridecafluoro-1,1,2,2-tetra-hydrodecyl triethoxysilane, 4-bromo-3,3,4,4-tetrafluorobutyltrichlorosilane, (heptadecafluoro-1,1,2,2-trtrahydrodecyl) methyldechlorosilane, Bis((tridecafluoro-1,1,2,2-tetrahydrooctyl)dimethylsiloxy)methylchlorosilane, 1H,1H,2H,2H-perfluorooctyl phosphonic acid | Tertiary perfluoroalkylamines (such as perfluorotri-n-pentylamine, FC-70 by 3M; perfluorotri-n-butylamine FC-40, etc), perfluoroalkylsulfides and perfluoroalkylsulfoxides, perfluoroalkylethers, perfluorocycloethers (like FC-77) and perfluoropolyethers (such as KRYTOX family of lubricants by DuPont), perfluoroalkylphosphines and perfluoroalkylphosphineoxides as well as their mixtures may be used for these applications, as well as their mixtures with perfluorocarbons and any and all members of the classes mentioned. | Any aqueous liquids and oils, or their complex mixtures |
| Silicon or Glass Trimethylchorosilane, Trisiloxane, 3-chloro-1,1,1,5,5,5-hexamethyl-3-[(trimethylsilyl)oxy]-, Acetoxyethylmethyldichlorosilane, Allyldimethylchlorosilane, 11-Bromoundecyldimethylchlorosilane | Water or aqueous liquids Hydrocarbons or their mixtures; Plant oils; Hydride Polydimethylsiloxane; Hydroxyl Polydimethylsiloxane; silicone oils, ionic liquids | Oils Water or aqueous liquids |

2. Self-Healing Coating Applications.

Owing to the physical robustness and self-healing capability of the self-healing coatings, the coatings of the present disclosure may be used as part of an article that requires a robust, liquid-repelling coating. Some examples include, but are not limited to, heat exchangers, anti-icing coatings, drag-reduction coatings, anti-fouling coatings, anti-graffiti coatings, anti-scaling coatings, coatings for optically transparent materials such as windows, and/or insect-repellent coatings.

In some embodiments, the article comprising the self-healing coating may repel a liquid. The repelled liquid may comprise high surface tension liquids and/or low surface tensions liquids, as well as solid substances. The high surface tension liquid may be water. The low surface tension liquid may be aqueous liquids comprising surfactants, organic solvents or combinations thereof. The repelled liquid may comprise complex fluids. The complex fluid may be a biological fluid. The complex fluid may be crude oil. The solid substances may comprise biological substances, non-biological substances, or combinations thereof. For example, a biological substance may be bacteria and/or insects, and a non-biological substance may be ice. The article comprising the self-healing coating may comprise a contact angle hysteresis for a repelled liquid less than 5°, less than 4°, less than 3°, less than 2° or less than 1°. The article comprising the self-healing coating may comprise a slide-off angle for a repelled liquid less than 5°, less than 4°, less than 3°, less than 2° or less than 1°.

A. Automobile Engine/Gear Box Oil Collection

The self-healing coatings may be applied on the interior of confined containers within automobiles, ships, and airplanes, such as engine and gear boxes for recycling or collection of engine/gear box oils or other functional oils. These confined containers are typically operated at elevated temperatures (e.g., 50-100° C.), and the self-healing coating may be healed directly when damaged by external means. The gear boxes are typically made of aluminum alloy with a roughened interior surface. In this application, the etching process may be excluded, and begin with submersion of the surface into 1H,1H,2H,2H-perfluorooctyl phosphonic acid dissolved with ethanol-water (9:1, volume ratio) solution at about 80° C. for about 1 hour. Then the surface may be lubricated with Krytox oil to form slippery coating.

B. Friction-reduction Coatings on Hypodermal Needles

The self-healing coatings may be applied on the exterior of hypodermal needles to reduce the tissue-to-needle friction, in order to enhance the needle placement accuracy for surgical operation (e.g., biopsy). When needed, the damaged chemical coatings may be heated to restore its surface hydrophobicity. The hypodermal needles may be made of stainless steel 304. The coating process may include three steps for this application. The first step is to etch the surface with ferric chloride acid for about 1 hour at room temperature. Then the etched needle may be further silane functionalized using (heptadecafluoro-1,1,2,2-tetra-hydrodecyl) trichlorosilane solution (1%, the ratio of silane and ethanol) as the second step. In the third step, the silanized needle may be lubricated with Dupont Krytox oil.

C. Anti-Icing Airfoils

The self-healing coatings may be applied onto airplane wings/helicopter blades for anti-icing purposes. When needed, the damaged self-healing coatings may be heated to restore its surface hydrophobicity. Airplane wings and helicopter blades are typically made of aluminum alloys, and the surface is not roughened with micro/nano structures. Wet chemical etching is suitable for these metal components; for example, etching may be performed with diluted chloride acid. The silane coating process may be performed as described above.

D. Friction Reduction Coating for Gears/Ball-Bearings

The self-healing coatings may be applied onto metal gears/ball-bearings for lubrication purposes. When needed, the damaged self-healing coatings may be heated to restore its surface hydrophobicity. Similar coating procedures may be performed as described above.

E. Drag Reduction/Anti-fouling Coating for Oil Pipeline/Ships

The self-healing coatings may be applied onto oil pipelines/ships for drag reduction purposes. When needed, the damaged self-healing coatings may be heated to restore its surface hydrophobicity. Similar coating procedures may be performed as described above.

F. Insect-Repellent Coatings for Airfoils

The self-healing coatings may be applied onto airfoils for insect-repellent purposes. The ability to prevent insects from sticking on the leading edge of the airfoils will maintain the aerodynamic shape of the airfoils, thereby preventing drag enhancement, and potential reduction in fuel consumption. When needed, the damaged self-healing coatings may be heated to restore its surface hydrophobicity. Similar coating procedures may be performed as described above.

3. Methods of Making the Self-Healing Coating

Provided herein are methods of producing a self-healing coating on a substrate. The methods may comprise applying a composition comprising silane molecules to at least a portion of the substrate to form a coating thereon, the silane molecules having a length and the coating having a thickness that is at least five times greater than the length of the silane molecules, the coating being self-healing such that when the coating is damaged to form a damaged portion, the damaged portion heals itself when exposed to a temperature of about 40° C. to about 400° C. for a period of time. The methods may further comprise lubricating the coating with a liquid or gaseous lubricant having affinity for the coating. Lubricating the coating may be performed by spraying, dip coating, spinning, rubbing from an oil-infused fabric, and combinations thereof. Additionally lubricating the coating may be performed by techniques commonly used within the art. The method may also comprise roughing the surface of the substrate. The method may further comprise alcohol. The silane coatings and lubricants listed above may be used in the method of making the self-healing coatings.

Typically, in embodiments comprising roughing the surface (e.g., roughened via an etching process), the roughened substrate becomes superhydrophilic. In some embodiments, the roughened surface is plasma-treated prior to adding the silane coating. The plasma treatment may activate hydroxyl groups on the surface of the substrate. To provide the silane coating on a roughened substrate, the silane deposition may be performed either in liquid or vapor phases through a time-controlled deposition. It may take from 1 hour to longer than several days, depending on the container size, solution volume, temperature, and ventilation condition. For example, the deposition may take at least 1 hour, at least 2 hours, at least 3 hours, at least 4 hours, at least 5 hours, at least 6 hours, at least 12 hours, at least 24 hours, at least 36 hours, at least 48 hours or at least 60 hours. The deposition may be performed at least at room temperature, at least 30° C., at least 40° C., at least 50° C., at least 60° C. or at least 70° C. The temperature may be less than 80° C., less than 70° C., less than 60° C., less than 50° C. or less than 40° C.

In some embodiments, the silane coating may be provided by immersing the substrate, with a roughened and/or unroughened surface, into a solution of silane and ethanol mixture (0.1-1% silane by volume), and the ethanol and silane may contact the substrate for 15±10 hours at room temperature. Higher temperatures may accelerate the silanization process.

The process of providing an excess silane layer (e.g., $L_{coating}$ is at least 2 times greater than $L_{mono}$) will form a layer on the surface of the substrate. To measure the thickness of the silane layer on the surface of the substrate, an atomic force microscope (AFM) may be used. The silane layer may have a thickness of from about 3 nm to about 10 μm. The silane layer may have a thickness of from about 10 nm to about 100 nm. For example, the thickness of the silane layer may be about 3 nm, about 4 nm, about 5 nm, about 6 nm, about 7 nm, about 8 nm, about 9 nm, about 10 nm, about 20 nm, about 30 nm, about 40 nm, about 50 nm, about 100 nm, about 200 nm, about 300, nm, about 400 nm, about 500 nm, about 1 μm, about 2 μm, about 3 μm, about 4 μm, about 5 μm, about 6 μm, about 7 μm, about 8 μm, about 9 μm, or about 10 μm. The thickness may be less than 10 μm, less than 9 μm, less than 8 μm, less than 7 μm, less than 6 μm, less than 5 μm, less than 4 μm, less than 3 μm, less than 2 μm, less than 1 μm, less than 500 nm, less than 400 nm, less than 300 nm, less than 200 nm, less than 100 nm, less than 50 nm, less than 40 nm, less than 30 nm, less than 20 nm, less than 10 nm, less than 9 nm, less than 8 nm, less than 7 nm, less than 6 nm, less than 5 nm, less than 4 nm, or less than 3 nm.

In some embodiments, an average silane thickness of 10 nm may support approximately 20 damage-healing cycles. Additionally, a thicker silane layer may provide more silane residues after each damage.

In some embodiments, the self-healing coating undergoes a heat treatment following the silane deposition on the substrate. Specifically, it has been found that heat treatment (e.g., 200° C.), after deposition of the silane coating, greatly enhances the performance of self-healing coatings. This is especially true for non-fluoro silanes. The heating treatment following silanization may enhance the uniformity of the silane coating on the surface. After lubrication of the silanized surface, the contact angle hysteresis of the liquid may be approximately 5° or less.

EXAMPLES

The foregoing may be better understood by reference to the following examples, which are presented for purposes of illustration and are not intended to limit the scope of the invention.

Example 1

Synthesis and Characterization of the Self-healing Coatings

Described below is the synthesis and characterization of the self-healing coatings. A schematic of the process is described in FIG. 1. The industrial materials coated with the thermally self-repairable coatings, include stainless steel 304, stainless steel 316, carbon steel, titanium, aluminum, copper, glass, polyethylene, polypropylene, polystyrene, ABS, and silicon, which were purchased from McMaster-Carr. The (Heptadecafluoro-1,1,2,2-tetrahydrodecyl) Trichlorosilane was purchased from Gelest Inc. This silane helps lower the surface tension on the industrial materials, and provides a source of hydrophobic "wax". The etchants used to roughen the surface were condensed hydrochloric acid, ferric chloride acid, sand paper, and sand. The lubricant Krytox oil (100 to 107) was purchased from DuPont.

To form micro/nano structures on the material surfaces, different etchants were used. The titanium surface provided nano-structures by condensed hydrochloric acid etching for 1 hour at 40° C. The stainless steel (304 and 316), carbon steel, copper surfaces were etched by ferric chloride acid for 1 hour at 40° C. to provide micro/nano structures. The aluminum surface was etched by water vapor at 100° C. for 10 to 15 min. For industrial metals, before the chemical etching process, they may be preliminarily roughened by sandpaper or sand blasting. In the case of glass, silicon, polyethylene, polypropylene, polystyrene, and ABS, the surfaces are roughened by sandpaper or sand blasting to form micro-structures.

Before functionalizing the surface, the industrial metals, glass, and silicon were cleaned by plasma for 10 min to activate the surface with more hydroxyl. The materials, which were etched with some roughness, were immersed into a silane solution, which was a mixture of (Heptadeca-fluoro-1,1,2,2-tetrahydrodecyl)Trichlorosilane and ethanol. The silane solution was 2 mM in ethanol. Concurrently, the solution was exposed to air. After the solution was evaporated, the surface chemical functionalization process was considered completed. Then the surface was lubricated with Krytox oil.

The self-healing coatings showed excellent repellency towards a variety of liquids from high surface tension liquid, such as water (~72.3 mN/m), to very low surface tension liquid, such as octane (~21.6 mN/m), as well as to a broad range of complex fluids. The measured contact angle hysteresis for these liquids was less than 3.5°, with a slide-off angle of less than 2° (FIGS. 11-15 and 24).

The XPS measurement was done using self-healing coatings on titanium by going through plasma cleaning and thermal self-healing processes. The first spectrum of elements in XPS was measured on the self-healing coating on titanium, which can form a slippery coating after lubricating the surface. The second spectrum was measured on the same titanium surface after 5 min of plasma cleaning. And the third spectrum was on the same titanium piece after 5 min of heating on a hot plate to self-heal. The XPS measurement was repeated on three different locations on the titanium surface. The measurement was repeated on another titanium surface, and the results were similar.

Figure 16:
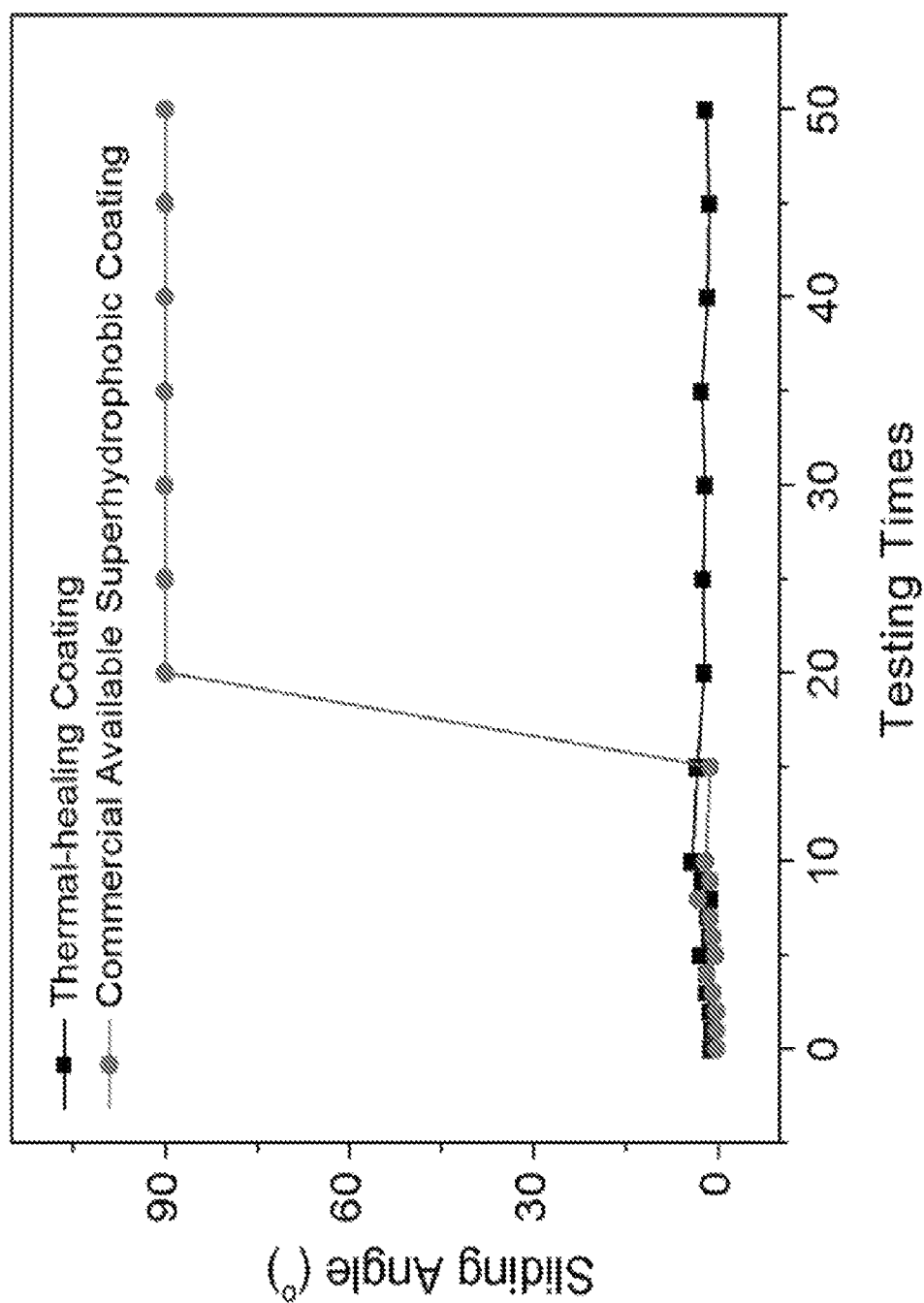
FIG. 16 shows robustness of one embodiment of the self-healing coating via sliding angle analysis as a function of tape-and-peel.
Figure 17:
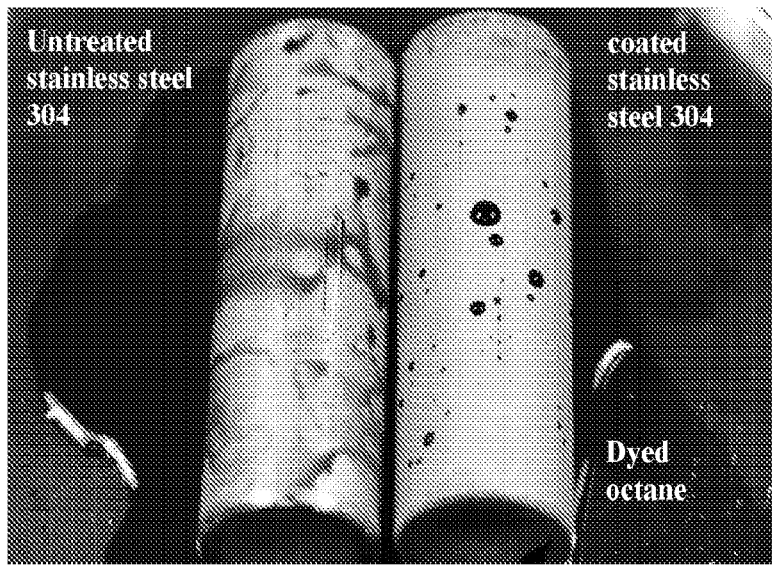
FIG. 17 depicts application of one embodiment of the self-healing coating, wherein the substrate comprises interior and exterior of a pipe section.
Figure 18:
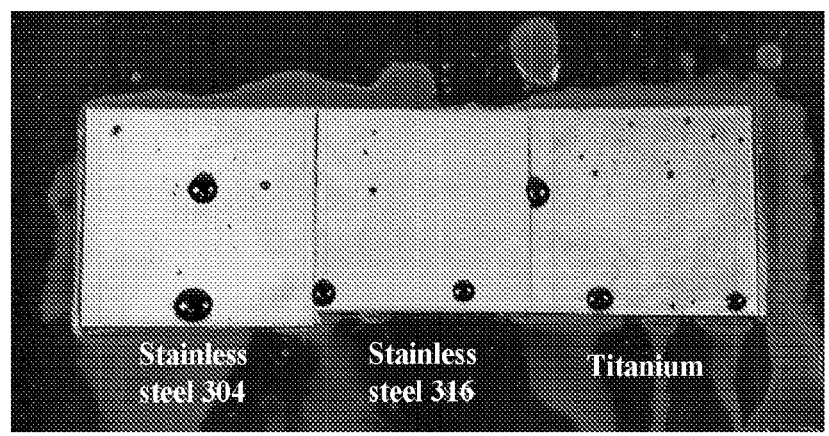
FIG. 18 depicts application of embodiment of the self-healing coating, wherein the substrate comprises a flat surface.
Figure 19:
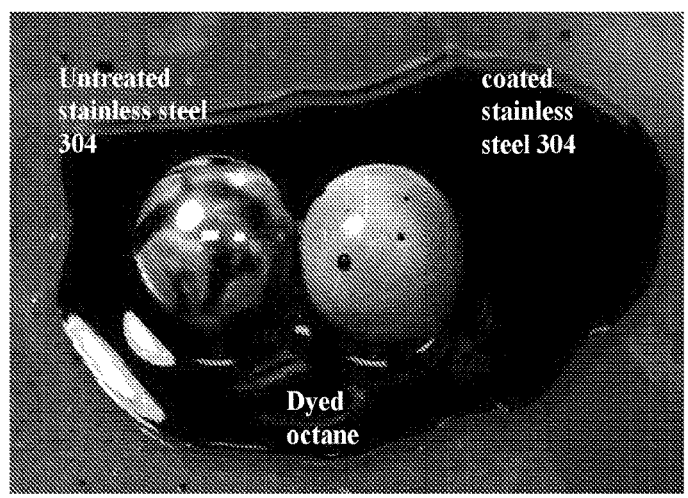
FIG. 19 depicts application of one embodiment of the self-healing coating, wherein the substrate comprises a sphere.
Figure 22:
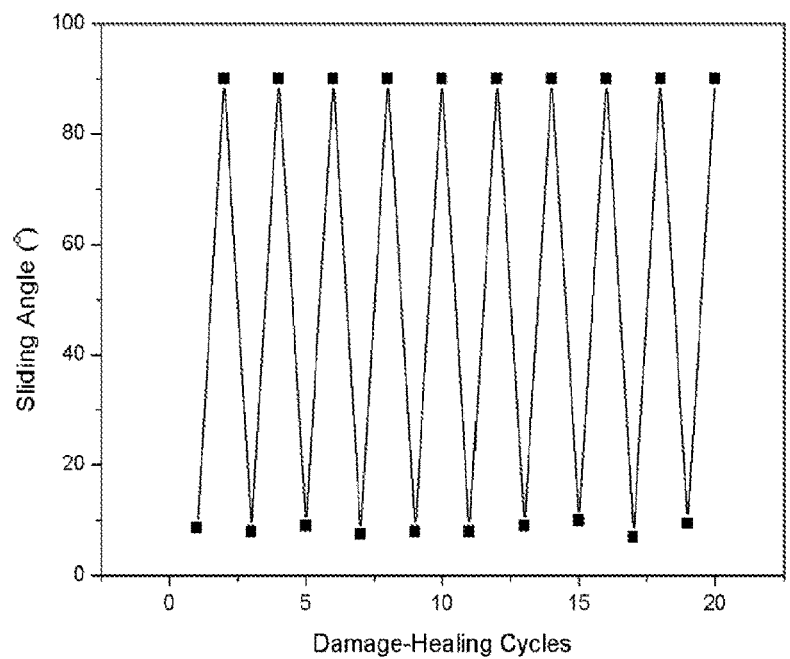
FIG. 22 shows the sliding angle analysis of the self-healing coating during damage and healing cycles.

Additionally, the self-healing coatings showed a very strong robustness, which may withstand at least 50 times pressure sensitive tape (e.g., Scotch® tape) attachment-and-detachment test with at least 0.5 N of weight, compared to a commercially available superhydrophobic coating, which can only resist approximately 15 times of the same pressure sensitive tape test (FIG. 16). Furthermore, the thermally healable silane coatings can be applied to different industrial metals, glass, and plastics, stainless steel 304, stainless steel 316, and titanium, but also carbon steel, copper, and aluminum, and different geometries (FIGS. 17-19 and 25-29). Furthermore, the self-healing coatings have exhibited the ability to self-heal, at least 20 times after being damaged. This is evidenced in FIG. 22, which shows the sliding angle being restored after the self-healing coating is healed.

Figure 3:
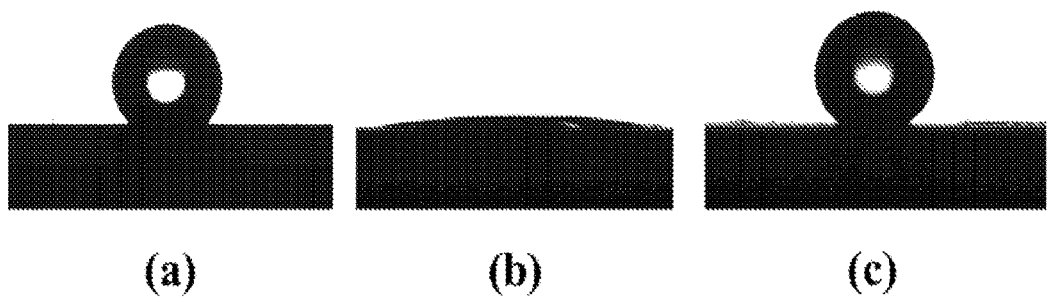
FIG. 3 shows one embodiment of the self-healing coating in contact with a repelled liquid, wherein the substrate comprises (a) self-healing coating, (b) damaged self-healing coating and (c) self-healed coating upon heating.
Figure 20:
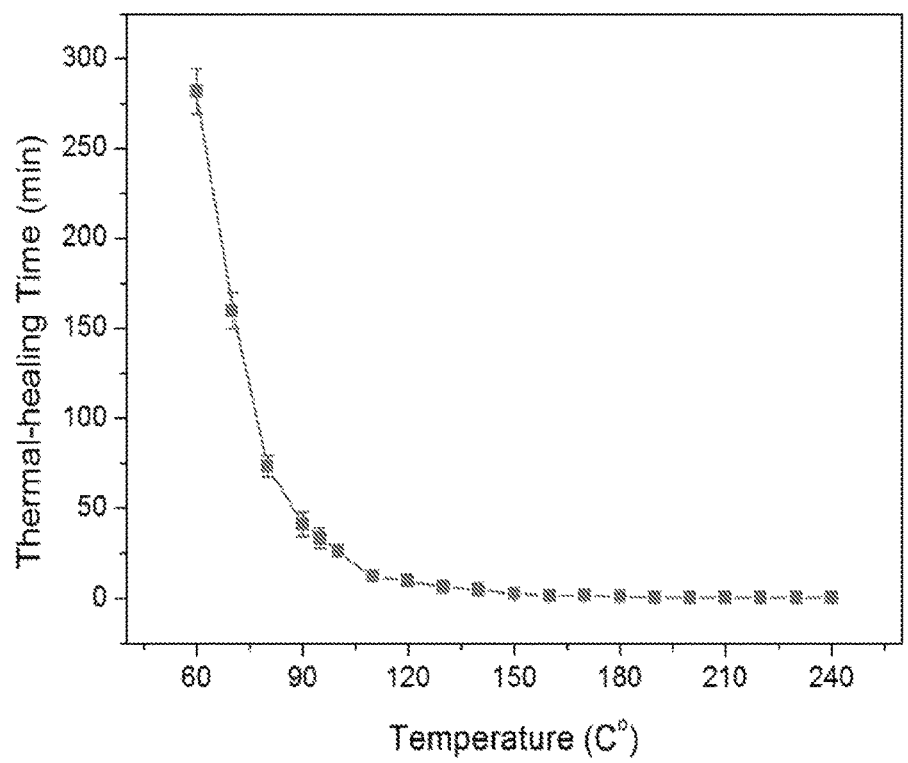
FIG. 20 shows the relationship between the self-healing time and temperature.
Figure 21:
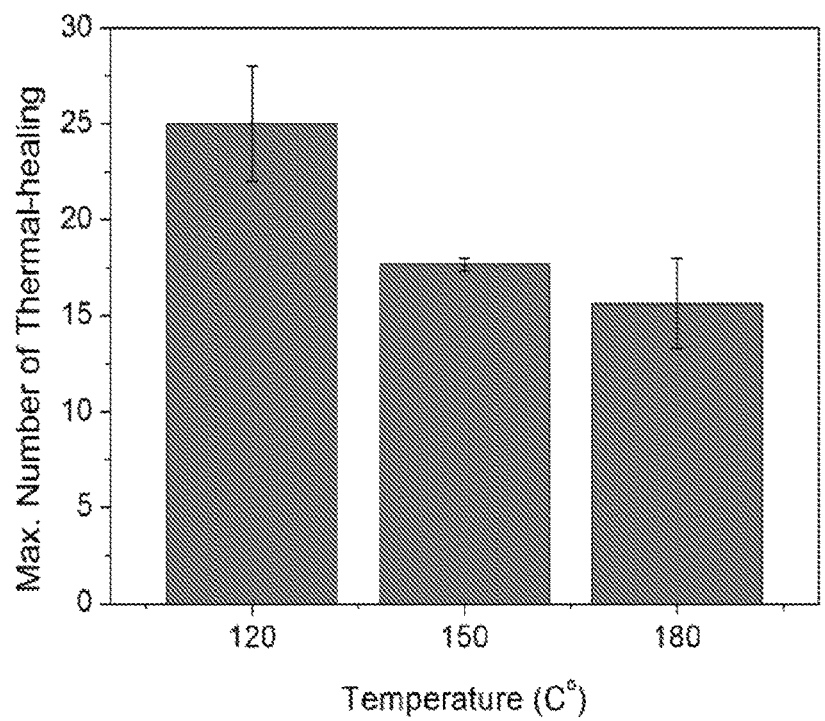
FIG. 21 shows the analysis of self-healing cycles at variable temperature ranges.

After chemical damage (e.g. reactive ion etching, plasma cleaning), or other physical damage, like rubbing and abrasion, the surface may be healed upon heating. The self-repairable property of the coatings is shown in FIGS. 20-21. The self-healing property of the coatings is also clearly demonstrated in FIG. 3. Starting from FIG. 3(*a*), the contact angle of the silanized titanium surface was 140°. After plasma cleaning the surface for 5 min, in FIG. 3(*b*), the surface became superhydrophilic with a contact angle less than 10°. FIG. 3(*c*) then shows that the coating was repaired by itself after heating up to 120±15° C. for 1-2 min; with a restored contact angle of 150°.

Figure 2:
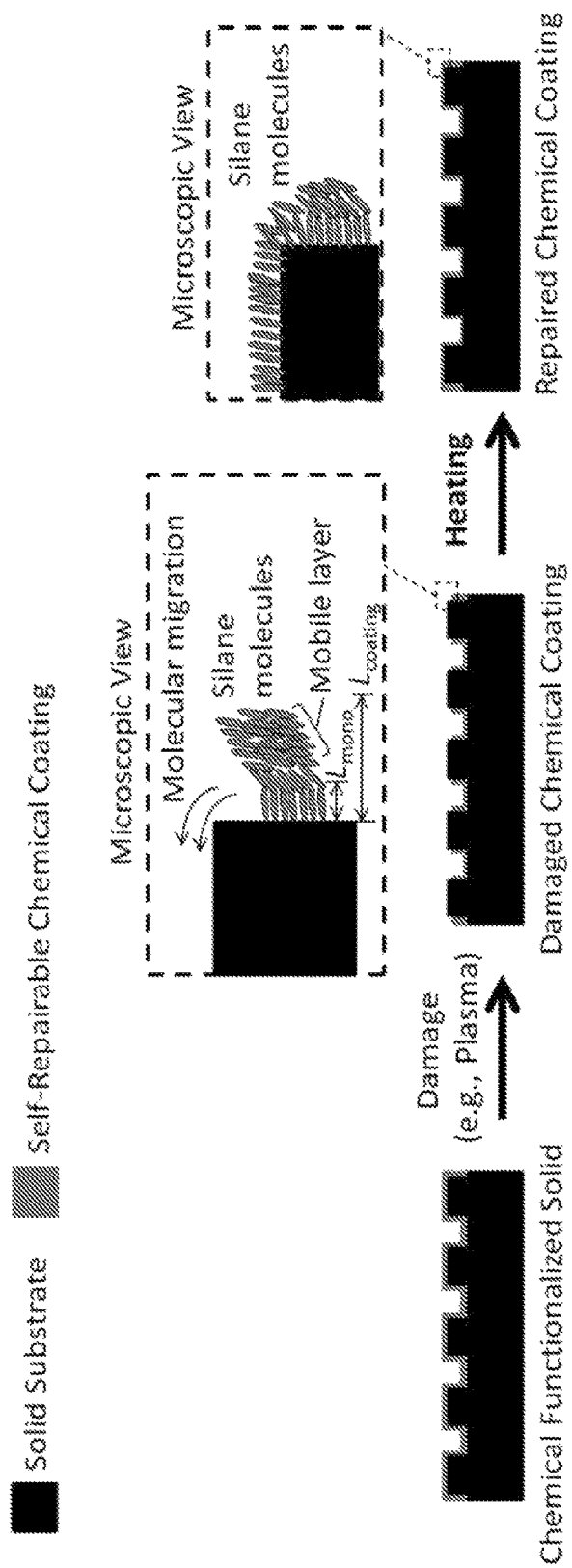
FIG. 2 is a schematic of the mechanism for the chemical self-repairing process.
Figure 4:
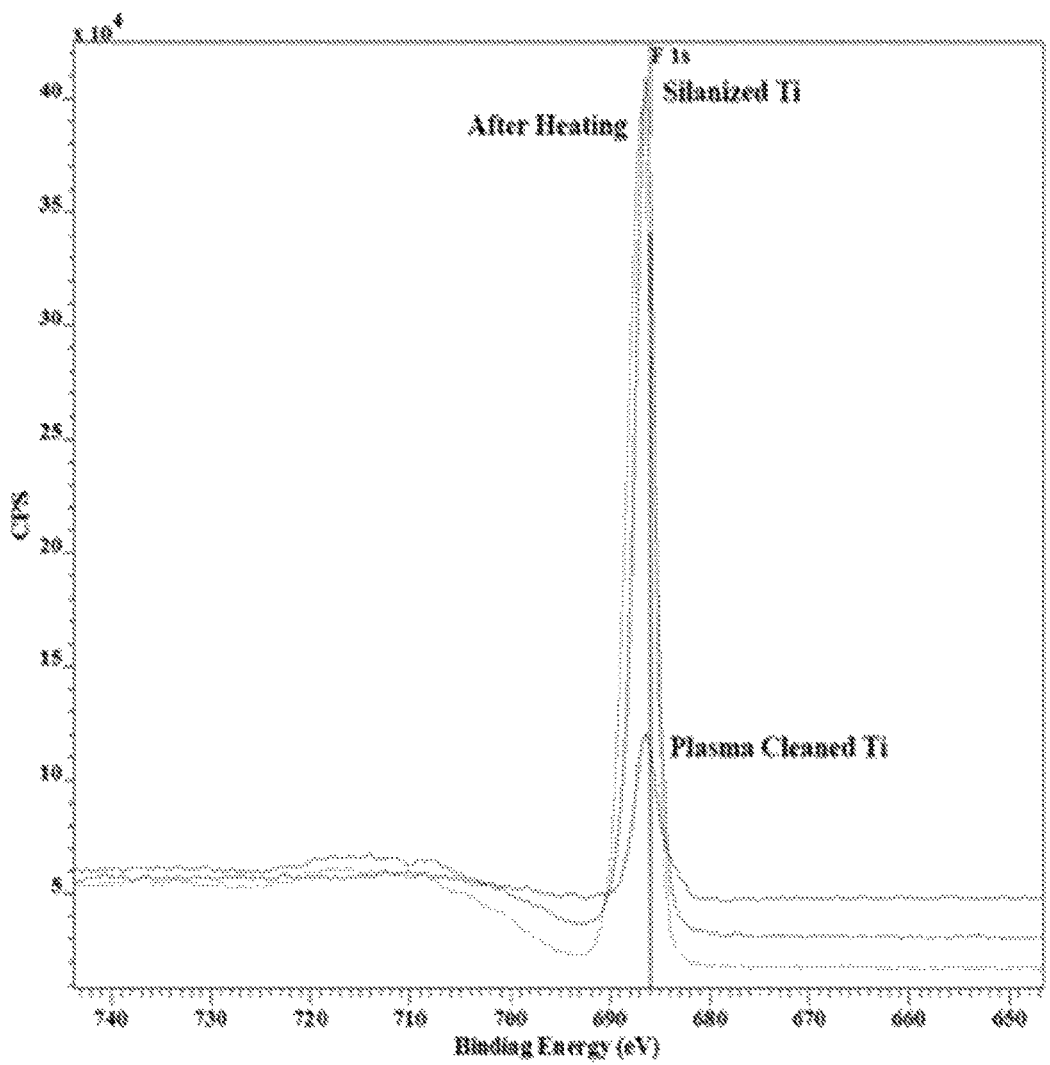
FIG. 4 shows XPS data exhibiting the level of fluorine surface concentrations in one embodiment of the self-healing coating.
Figure 5:
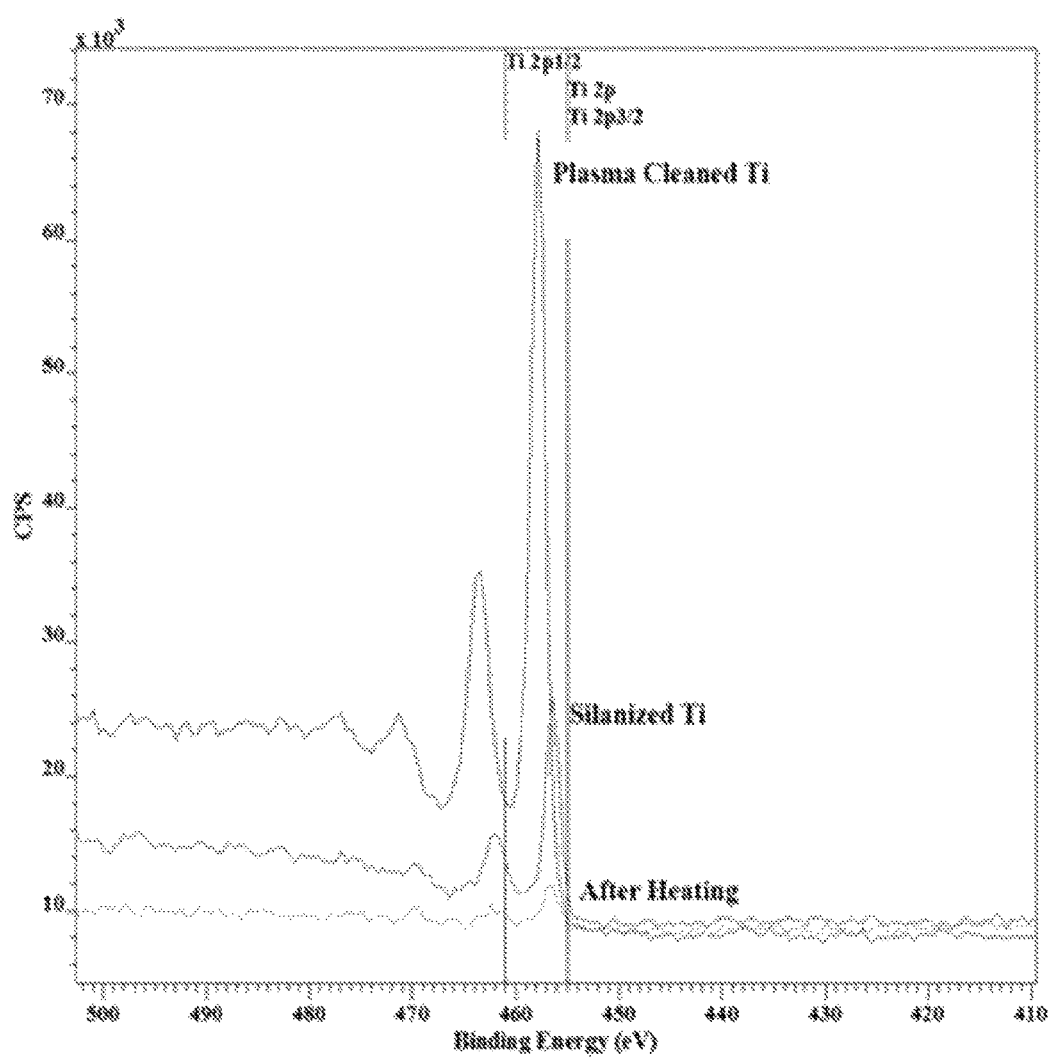
FIG. 5 shows XPS data showing the level of titanium surface concentrations in one embodiment of the self-healing coating following plasma treatment.
Figure 6:
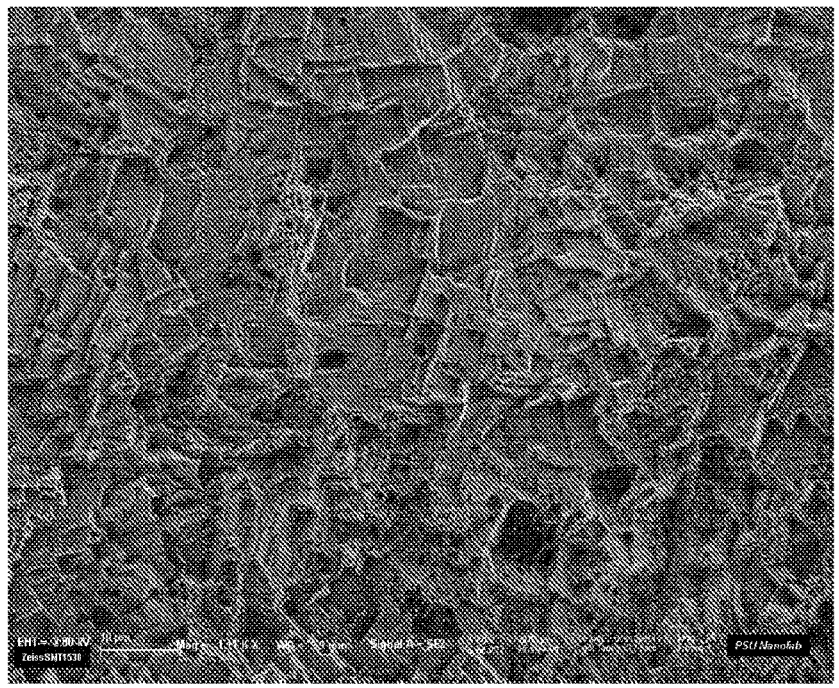
FIG. 6 shows an electron micrograph showing the micro and nanoscale topography of etched stainless steel 304 (scale bar 10 μm).
Figure 7:
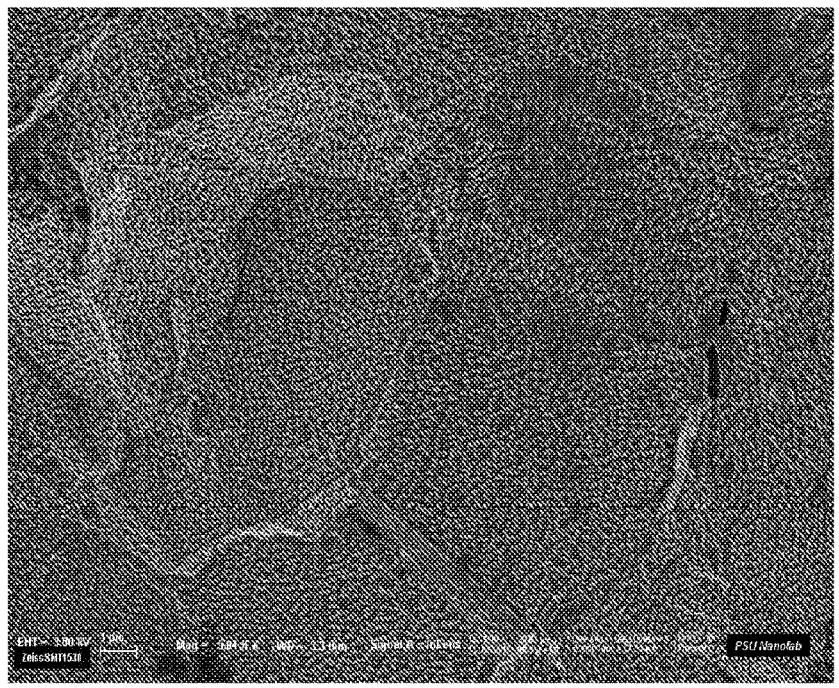
FIG. 7 shows an electron micrograph showing the micro and nanoscale topography of titanium (scale bar 1 μm).
Figure 8:
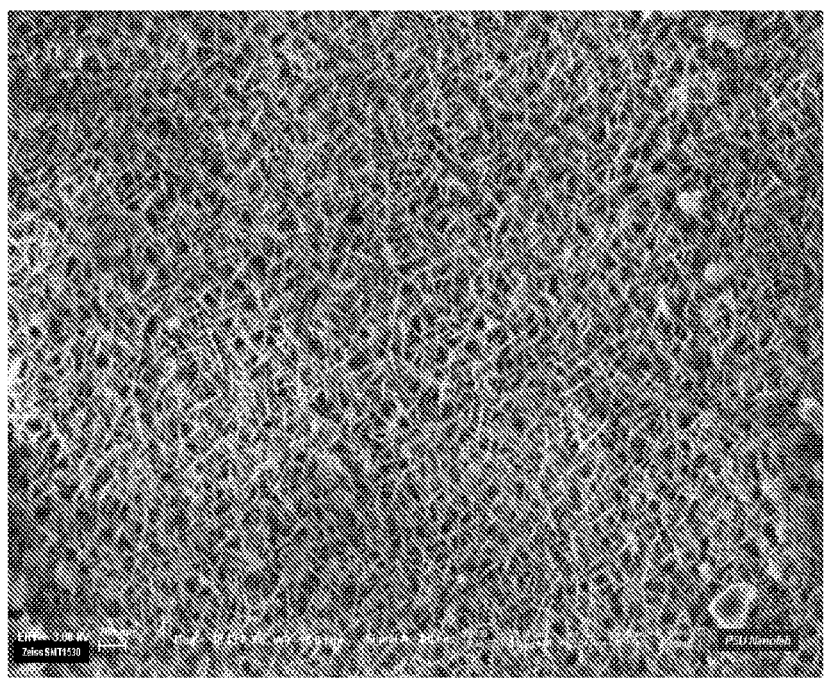
FIG. 8 shows an electron micrograph showing the micro and nanoscale topography of aluminum (scale bar 200 nm).
Figure 9:
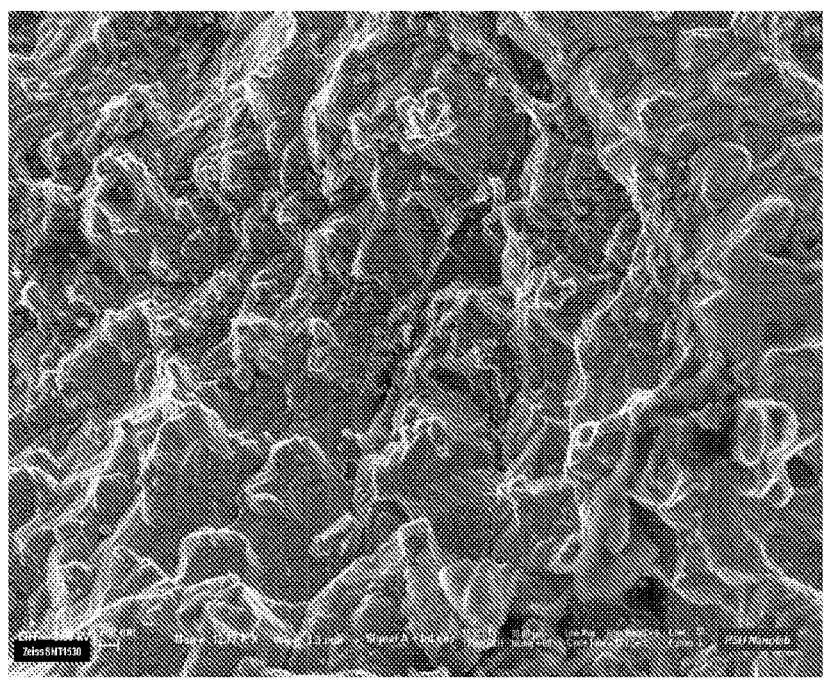
FIG. 9 shows an electron micrograph showing the micro and nanoscale topography of copper (scale bar 200 nm).
Figure 10:
FIG. 10 shows an electron micrograph showing the micro and nanoscale topography of carbon steel (scale bar 3 μm).
Figure 11:
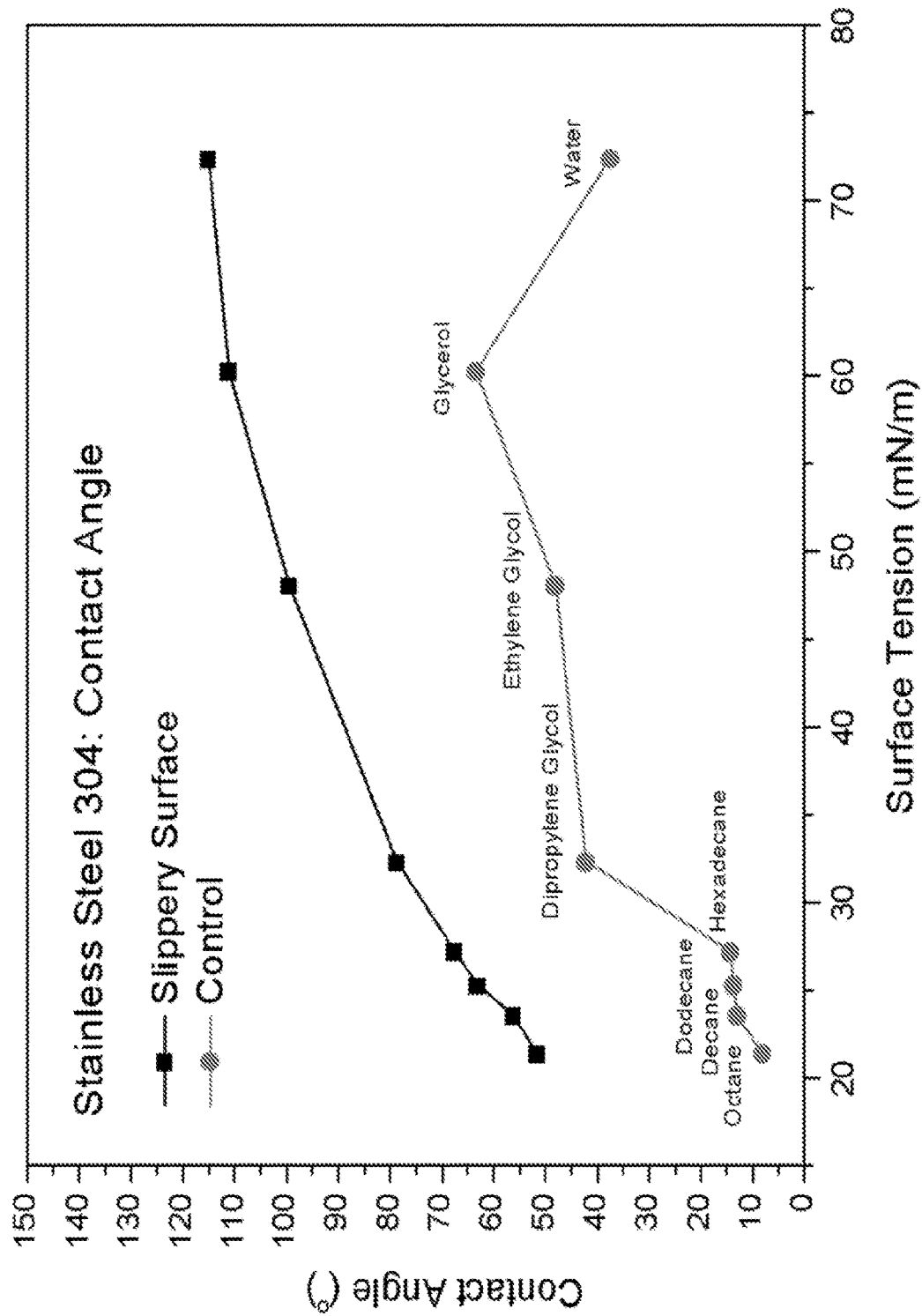
FIG. 11 shows contact angle analysis, wherein stainless steel 304 is the substrate.
Figure 12:
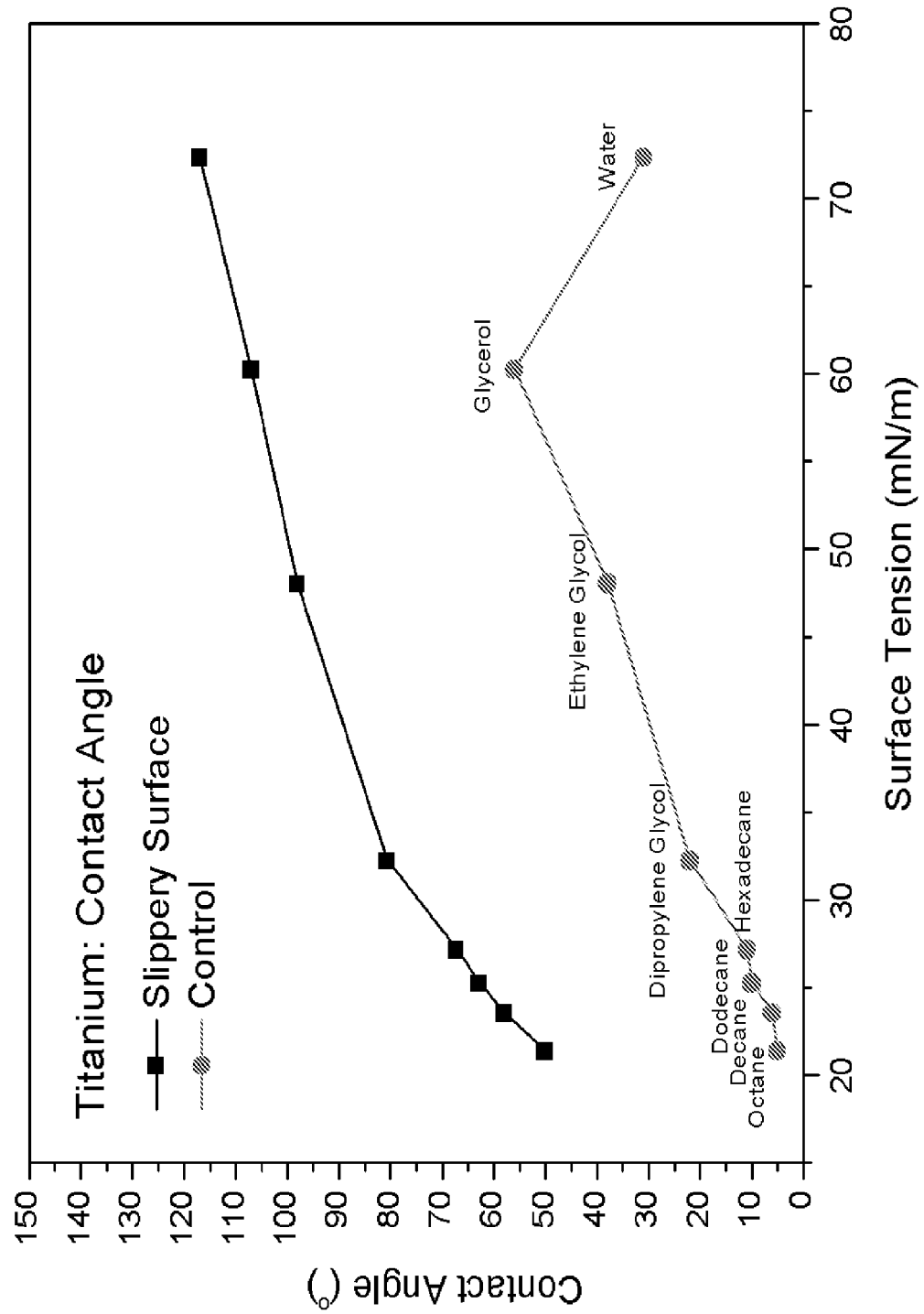
FIG. 12 shows contact angle analysis, wherein titanium is the substrate.
Figure 13:
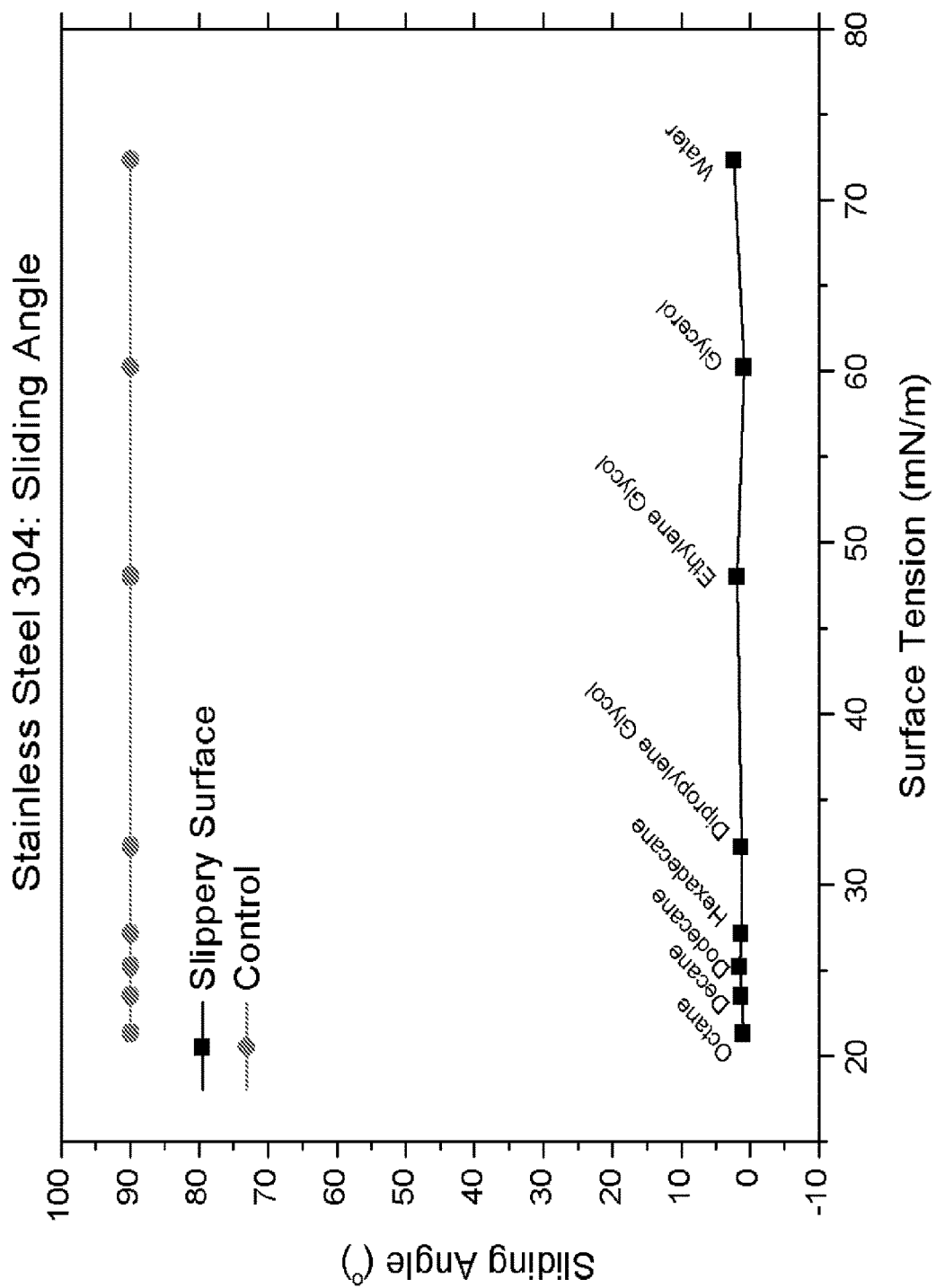
FIG. 13 shows sliding angle analysis, wherein stainless steel 304 is the substrate.
Figure 14:
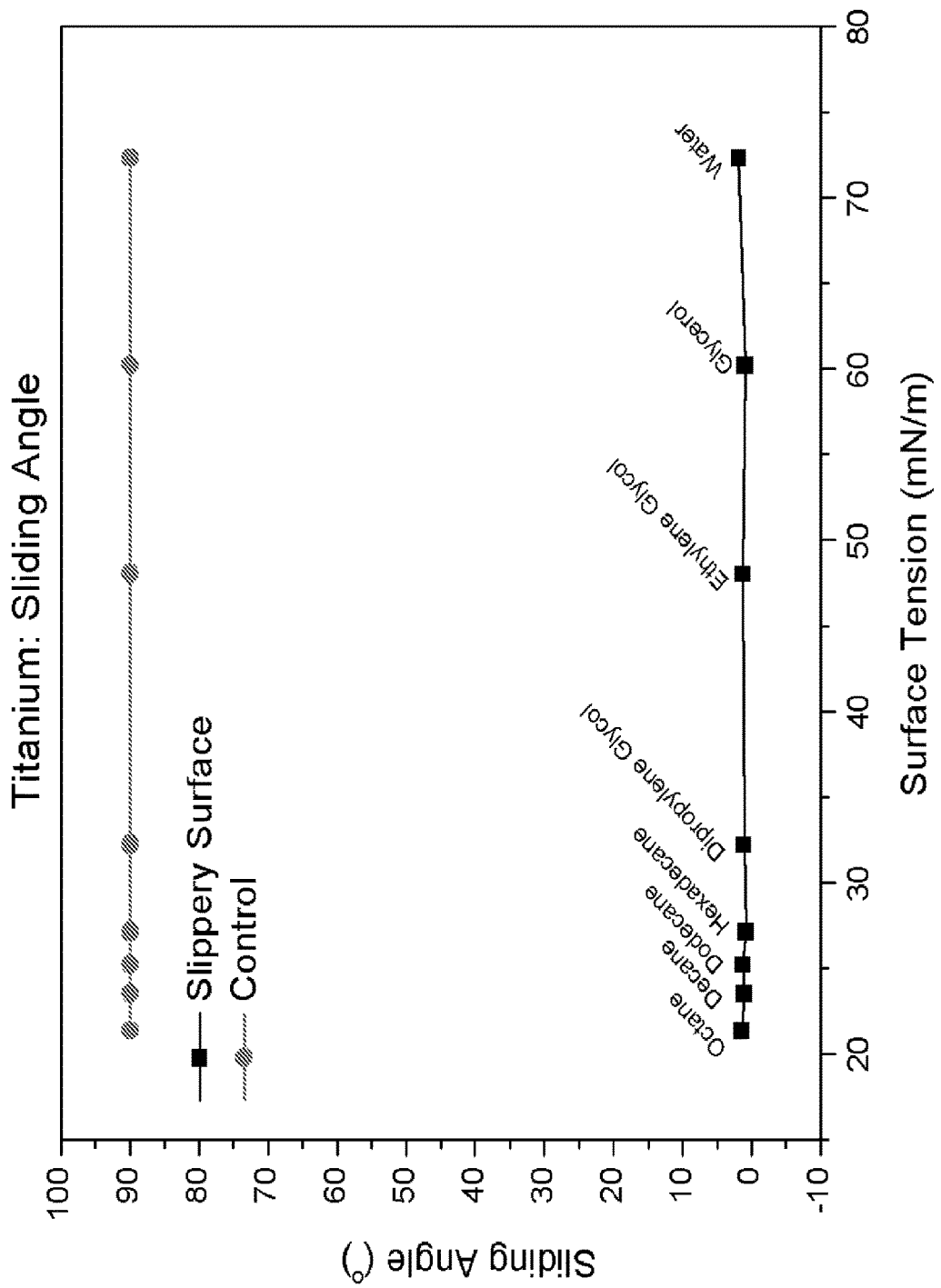
FIG. 14 shows sliding angle analysis, wherein titanium is the substrate.
Figure 15:
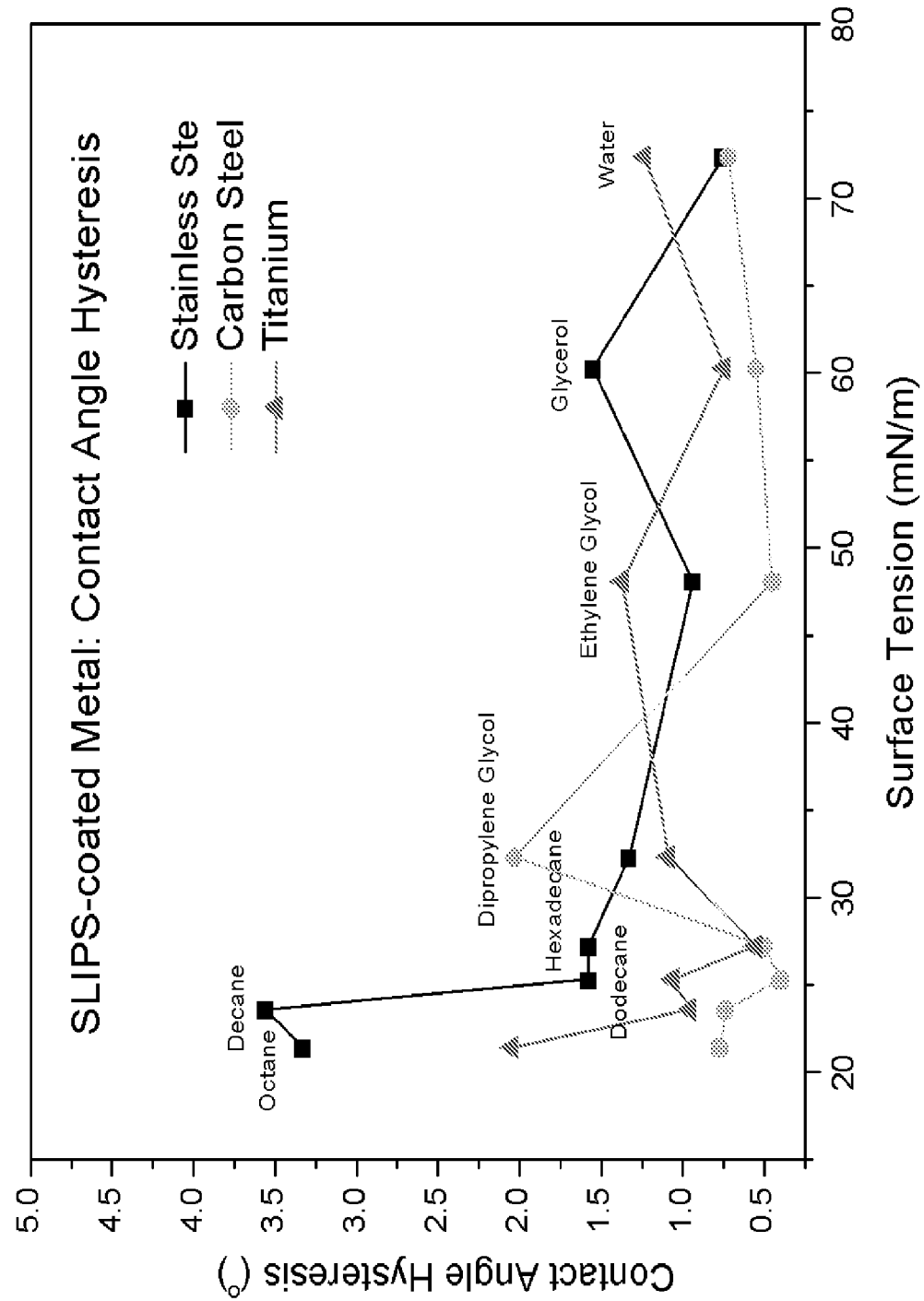
FIG. 15 shows liquid-repellent characteristics of different metal-based substrates coated with one embodiment of the self-healing coating.

In the XPS data of FIGS. 4 and 5, the silane layer covered the whole surface in silanized titanium and self-repaired titanium, but only covered partial regions of the surface in plasma cleaned titanium. Since titanium itself is hydrophilic, and the titanium sample had micro- and nano-structures on the surface, it is suggested by the XPS data that plasma cleaning removed a thin layer of silane, and exposed the titanium substrate to air. Additionally, in FIG. 4, there was still some fluorine left on the surface after plasma cleaning, which suggests that the silane was left on the surface. Based on the structures of the titanium sample, the self-repairable property of the coating may be described as a silane migration mechanism, shown in FIG. 2. After silanization, the surface is covered by a silane layer, which is hydrophobic. Then the surface turns into superhydrophilic with plasma cleaning. The residual silane remains in the valleys, and is removed in the peaks. By heating up to approximately 120° C., the silane molecules gain energy and migrate from the valley to the peak. Accordingly, the surface recovers its hydrophobicity.

Figure 23:
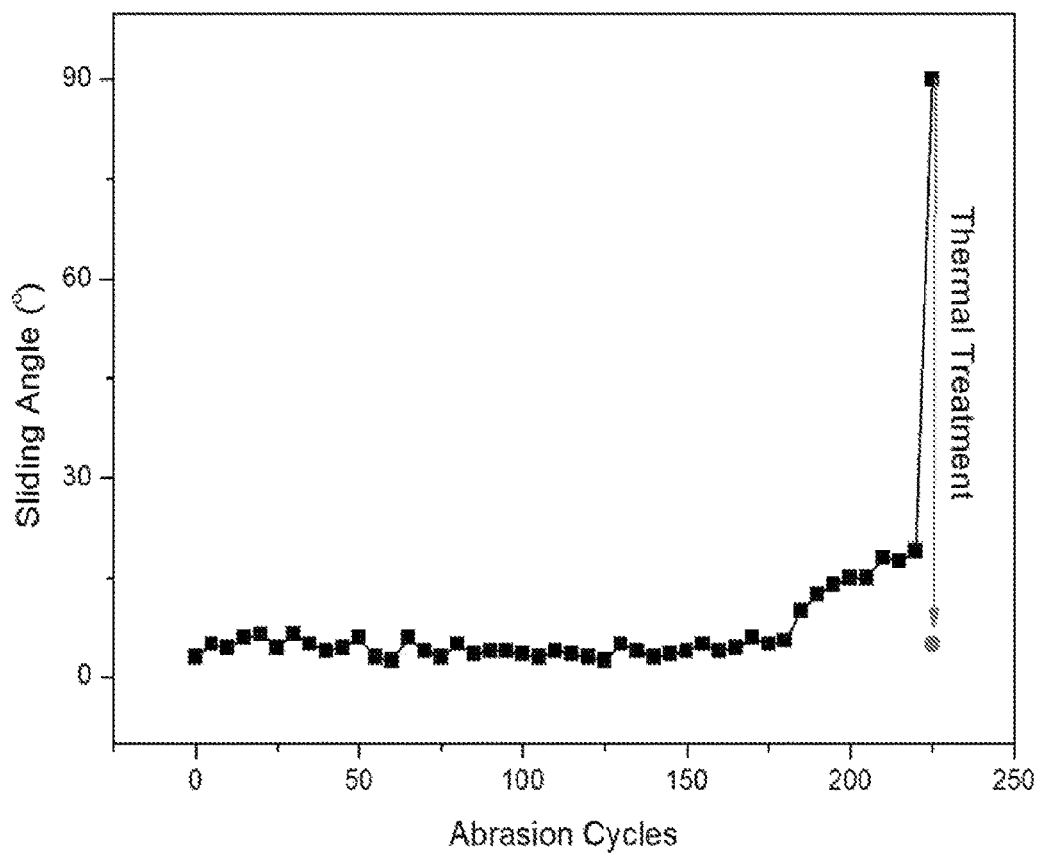
FIG. 23 shows liquid-repellent characteristics of the self-healing coating (with lubricant) under an increasing number of abrasive cycles.
Figure 24:
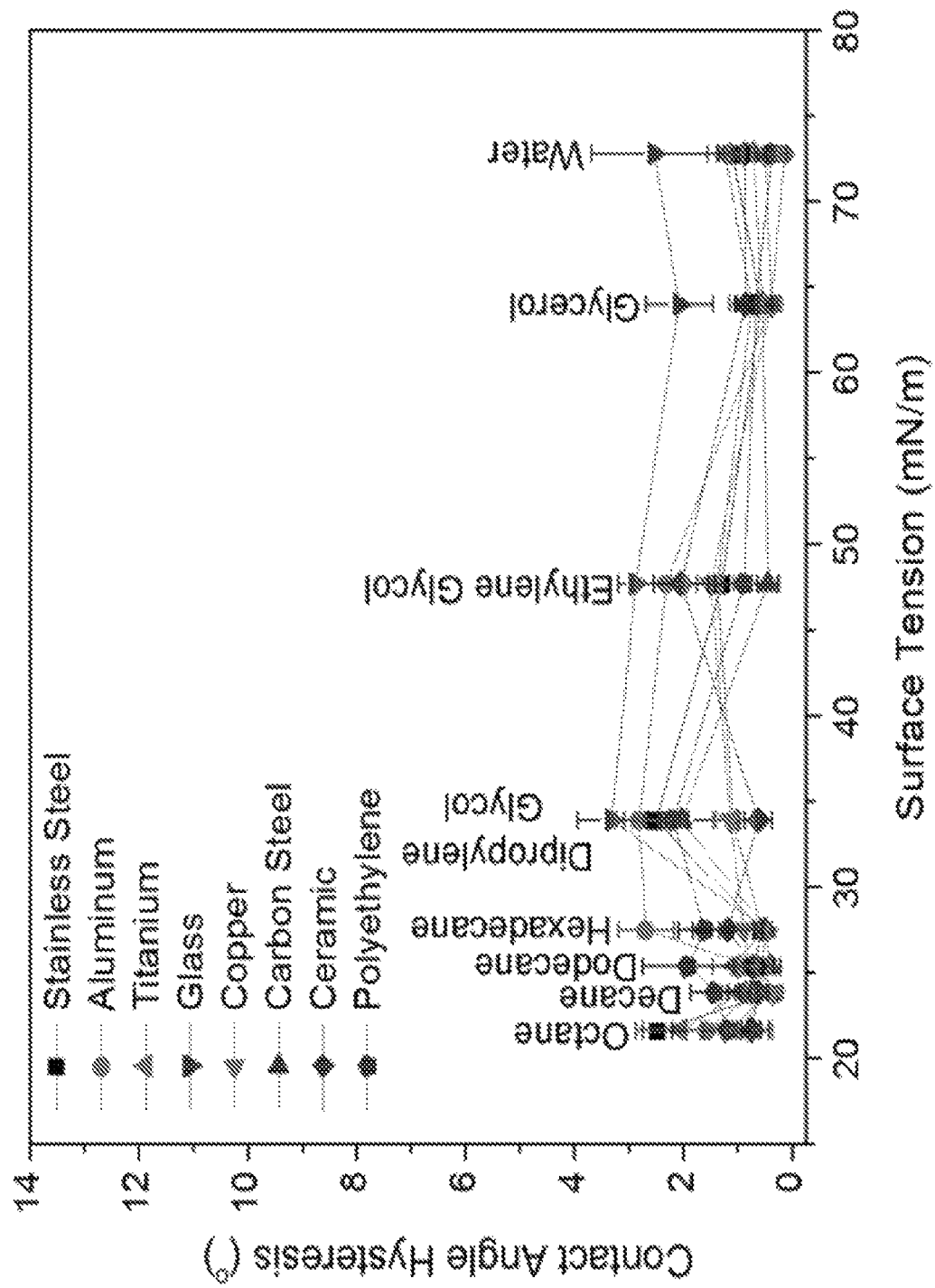
FIG. 24 shows liquid-repellent characteristics of different substrates coated with one embodiment of the self-healing coating.
Figure 25:
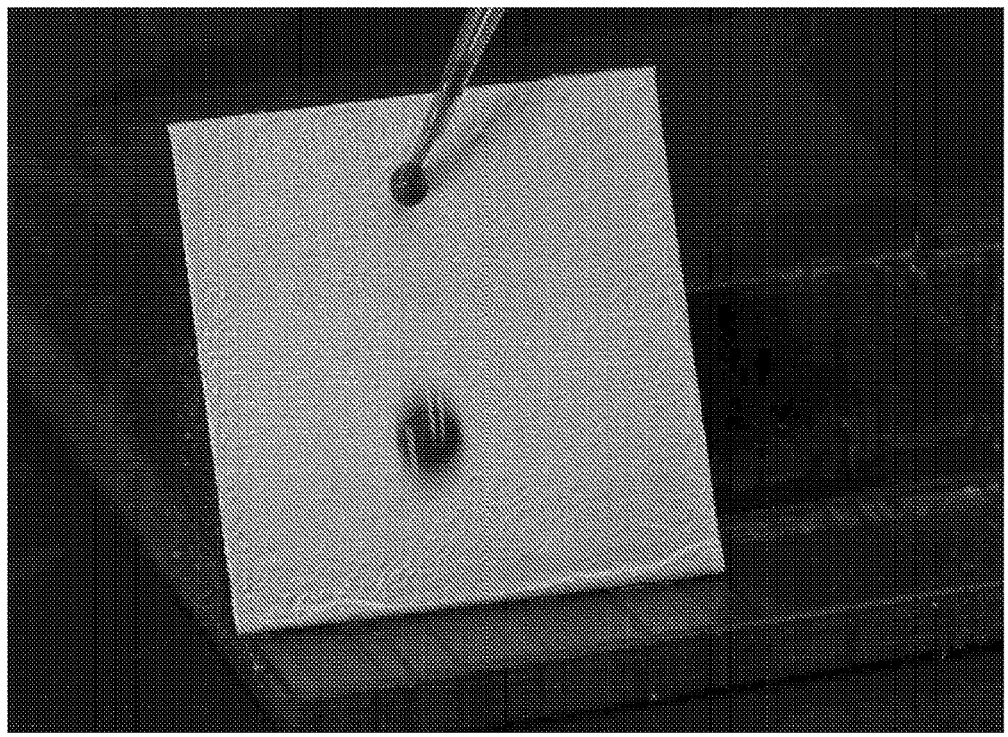
FIG. 25 depicts application of one embodiment of the self-healing coating on copper.
Figure 26:
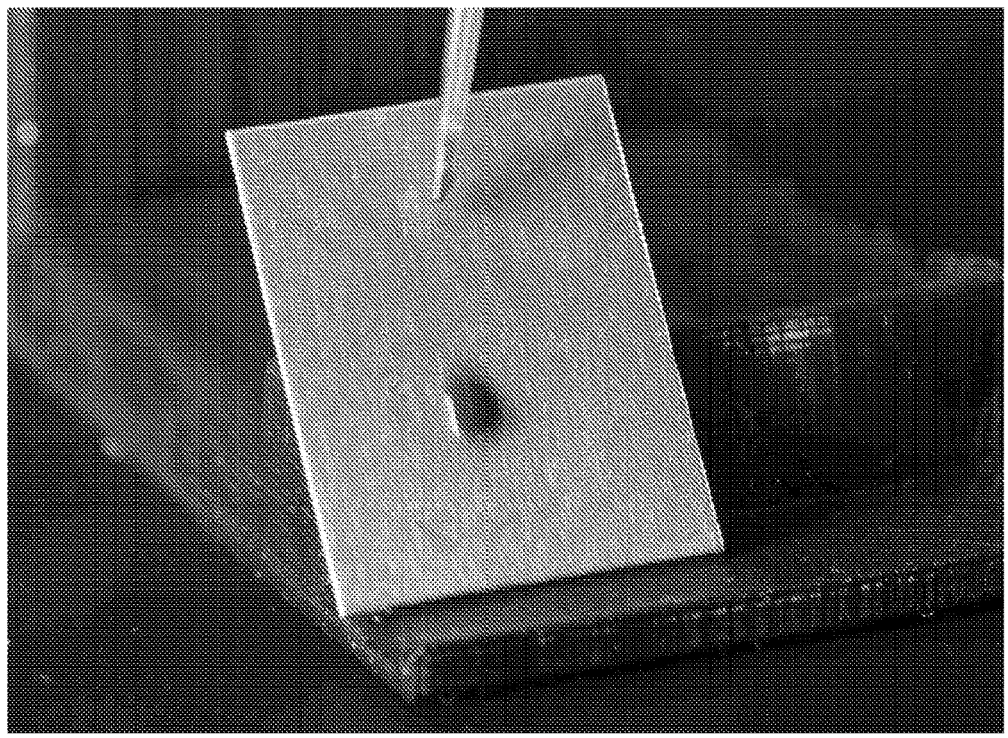
FIG. 26 depicts application of one embodiment of the self-healing coating on aluminum.
Figure 27:
FIG. 27 depicts application of one embodiment of the self-healing coating on glass.
Figure 28:
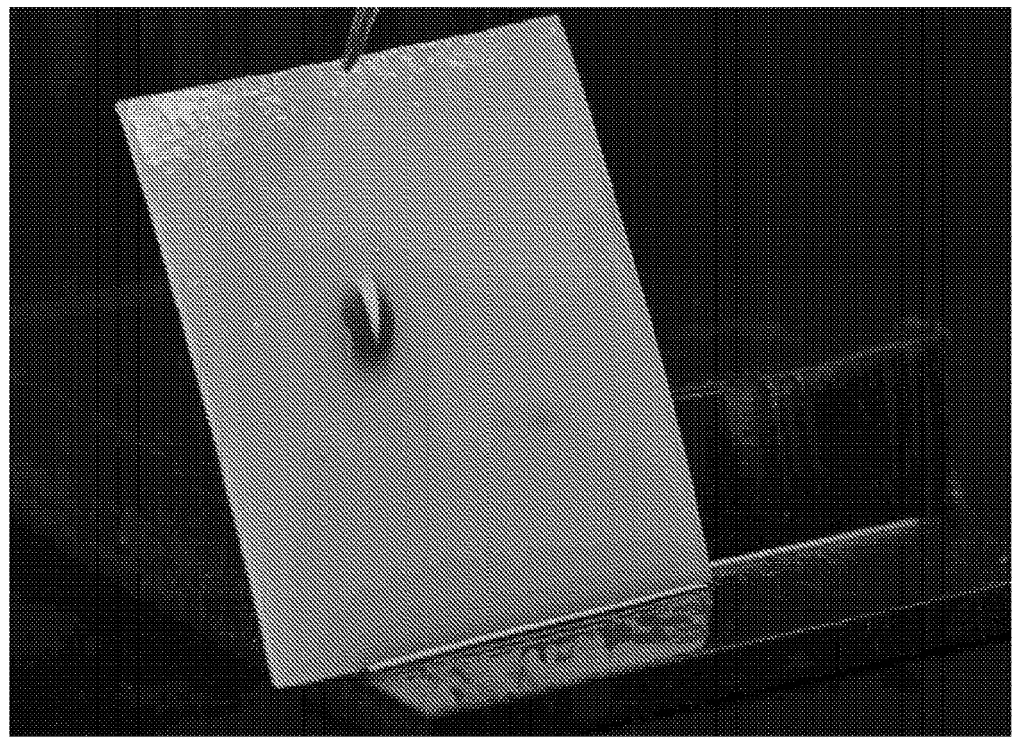
FIG. 28 depicts application of one embodiment of one embodiment of the self-healing coating on polyethylene.
Figure 29:
FIG. 29 depicts application of one embodiment of the self-healing coating on ceramic.

The thermal healing of the coating may occur with or without lubrication. In FIG. 23, the silanized aluminum was lubricated with a perfluorinated oil, and physically abraded by sandpaper under the force of 10 N. A sliding angle was measured after each 5 cycles of abrasion with 20 nt of decane droplet. After 225 cycles, the sliding angle of a decane droplet went from around 5° to 90°. After this damage, the surface is heated to 180° C. for 3 min to self-heal the silane coating. After the thermal treatment, the surface was repaired and repelled a decane droplet at a sliding angle of 5°.

What is claimed is:
1. An article comprising:
    (a) a substrate;
    (b) a self-healing coating directly adhered to the substrate, the self-healing coating comprising silane molecules having a length and the coating having a thickness at least five times greater than the length of the silane molecules and from 1 μm to about 10 μm; and
    (c) a lubricant,
    wherein the coating is self-healing such that when the coating includes a damaged portion, the damaged portion is healed when it is exposed to a temperature of about 40° C. to about 400° C.
2. The article of claim 1, wherein the lubricant does not form an interface with the substrate.
3. The article of claim 1, wherein the substrate comprises a roughened surface.
4. The article of claim 1, wherein a portion of the self-healable coating is covalently bonded to the substrate.
5. The article of claim 1, wherein the damaged portion comprises a portion from which the lubricant and the self-healing coating have been removed from the substrate.
6. The article of claim 1, wherein the article has repellency to liquids.
7. The article of claim 6, wherein the liquid is water.
8. The article of claim 1, wherein the article has repellency to an aqueous liquid comprising at least one of a surfactant and an organic liquid.

9. The article of claim 1, wherein the article has a contact angle hysteresis for a repelled liquid less than about 5°.

10. The article of claim 1, wherein the article has a slide-off angle for a repelled liquid less than about 5°.

11. The article of claim 1, wherein the article may withstand at least 50 pressure sensitive tape attachment-and-detachment tests with at least a force of 0.5 N.

12. The article of claim 1, wherein the silane molecule is selected from (heptadecafluoro-1,1,2,2-tetra-hydrodecyl), trichlorosilane, tridecafluoro-1,1,2,2-tetra-hydrodecyl triethoxysilane, 4-bromo-3,3,4,4-tetrafluorobutyltrichlorosilane, (heptadecafluoro-1,1,2,2-tetrahydrodecyl)methyldechlorosilane, 1H,1H,2H,2H-perfluorooctyl phosphonic acid(3-heptafluotoisopropoxy)propyltrichlorosilane, (3-Chloropropyl)trimethoxysilane, octadecyltrichlorosilane, nonafluoro hexyl trimethoxysilane, heptadecaflourodecyltrimethoxysilane, octadecyldimethylchlorosilane, octyldimethylchlorosilane, dimethyldichlorosilane, butyldimethylchlorosilane, trimethylchlorosilane and combinations thereof.

13. The article of claim 1, wherein the lubricant is selected from tertiary perfluoroalkylamines, perfluoroalkylsulfides, perfluoroalkylsulfoxides, perfluoroalkylethers, perfluorocycloethers, perfluoropolyethers, perfluoroalkylphosphines, perfluoroalkylphosphineoxides, mineral oils, plant oils, ionic liquids, liquid polydimethysiloxane, water, aqueous liquids, hydrocarbons and combinations thereof.

14. A method for producing a self-healing coating on a substrate, the method comprising:
(a) applying a composition comprising silane molecules directly to at least a portion of the substrate to form a coating thereon, the silane molecules having a length and the coating having a thickness that is at least five times greater than the length of the silane molecules and from 1 μm to about 10 μm, the coating being self-healing such that when the coating is damaged to form a damaged portion, the damaged portion heals itself when exposed to a temperature of about 40° C. to about 400° C.; and
(b) lubricating the coating with a liquid or gaseous lubricant having affinity for the coating.

15. The method of claim 14, further comprising roughening a surface of the substrate.

16. The method of claim 14, wherein the silane molecule is selected from (heptadecafluoro-1,1,2,2-tetra-hydrodecyl), trichlorosilane, tridecafluoro-1,1,2,2-tetra-hydrodecyl triethoxysilane, 4-bromo-3,3,4,4-tetrafluorobutyltrichlorosilane, (heptadecafluoro-1,1,2,2-tetrahydrodecyl)methyldechlorosilane, 1H,1H,2H,2H-perfluorooctyl phosphonic acid(3-heptafluotoisopropoxy)propyltrichlorosilane, (3-Chloropropyl)trimethoxysilane, octadecyltrichlorosilane, nonafluoro hexyl trimethoxysilane, heptadecaflourodecyltrimethoxysilane, octadecyldimethylchlorosilane, octyldimethylchlorosilane, dimethyldichlorosilane, butyldimethylchlorosilane, trimethylchlorosilane and combinations thereof.

17. The method of claim 14, wherein the lubricant is selected from tertiary perfluoroalkylarnines, perfluoroalkylsulfides, perfluoroalkylsulfoxides, perfluoroalkylethers, perfluorocycloethers, perfluoropolyethers, perfluoroalkylphosphines, perfluoroalkylphosphineoxides, mineral oils, plant oils, ionic liquids, liquid polydimethysiloxane, water, aqueous liquids, and hydrocarbons, and combinations thereof.

18. The method of claim 14, further comprising self-healing a damaged portion of the coating by exposing the coating to a temperature of about 40° C. to about 400° C.

19. An article comprising:
(a) a substrate; and
(b) a self-healing coating directly adhered to the substrate, the self-healing coating comprising silane molecules having a length and the coating having a thickness at least five times greater than the length of the silane molecules and from 1 μm to about 10 μm,
wherein the coating is self-healing such that when the coating includes a damaged portion, the damaged portion is healed when it is exposed to a temperature of about 40° C. to about 400° C.

20. The article of claim 19, further comprising a lubricant, wherein the lubricant is selected from tertiary perfluoroalkylamines, perfluoroalkylsulfides, perfluoroalkylsulfoxides, perfluoroalkylethers, perfluorocycloethers, perfluoropolyethers, perfluoroalkylphosphines, perfluoroalkylphosphineoxides, mineral oils, plant oils, ionic liquids, liquid polydimethysiloxane, water, aqueous liquids, and hydrocarbons, and combinations thereof; and
wherein the silane molecule is selected from (heptadecafluoro-1,1,2,2-tetra-hydrodecyl), trichlorosilane, tridecafluoro-1,1,2,2-tetra-hydrodecyl triethoxysilane,4-bromo-3,3,4,4-tetrafluorobutyltrichlorosilane, (heptadecafluoro-1,1,2,2-tetrahydrodecyl)methyldechlorosilane, 1H,1H,2H,2H-perfluorooctyl phosphonic acid(3-heptafluotoisopropoxy)propyltrichlorosilane, (3-Chloropropyl)trimethoxysilane, octadecyltrichlorosilane, nonafluoro hexyl trimethoxysilane, heptadecaflourodecyltrimethoxysilane, octadecyldimethylchlorosilane, octyldimethylchlorosilane, dimethyldichlorosilane, butyldimethylchlorosilane, trimethylchlorosilane and combinations thereof.

* * * * *